(12) United States Patent
Green et al.

(10) Patent No.: US 7,693,570 B2
(45) Date of Patent: *Apr. 6, 2010

(54) MAGNETIC RESONANCE IMAGING WITH ADJUSTABLE FIXTURE APPARATUS

(75) Inventors: Charles A. Green, Holbrook, NY (US); Jan Votruba, Ridge, NY (US)

(73) Assignee: Fonar Corporation, Melville, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/427,443

(22) Filed: May 1, 2003

(65) Prior Publication Data

US 2004/0030241 A1 Feb. 12, 2004

Related U.S. Application Data

(63) Continuation-in-part of application No. 10/131,843, filed on Apr. 25, 2002, now Pat. No. 7,551,954.

(51) Int. Cl.
*A61B 5/055* (2006.01)

(52) U.S. Cl. .................... 600/415; 600/422; 5/601; 5/621; 324/318

(58) Field of Classification Search ............ 600/410, 600/411, 415, 422, 427; 324/318, 322, 307, 324/309; 5/601, 610, 611, 621–624
See application file for complete search history.

(56) References Cited

U.S. PATENT DOCUMENTS

| | | |
|---|---|---|
| 4,411,270 A | 10/1983 | Damadian |
| 4,629,989 A | 12/1986 | Riehl et al. |
| 4,891,596 A | 1/1990 | Mitomi et al. |
| 4,943,775 A | 7/1990 | Boskamp et al. |
| 4,968,937 A | 11/1990 | Akgun |
| 4,985,678 A | 1/1991 | Gangarosa et al. |
| 5,008,624 A | 4/1991 | Yoshida |
| 5,066,915 A | 11/1991 | Omori et al. |
| 5,085,219 A | 2/1992 | Ortendahl et al. |
| 5,221,902 A * | 6/1993 | Jones et al. .................. 600/422 |
| 5,274,332 A * | 12/1993 | Jaskolski et al. ............. 324/318 |
| 5,307,806 A * | 5/1994 | Jones .......................... 600/422 |
| 5,473,251 A * | 12/1995 | Mori ........................... 324/318 |
| 5,519,321 A | 5/1996 | Hagen et al. |

(Continued)

FOREIGN PATENT DOCUMENTS

DE 38 19 541 12/1988

(Continued)

OTHER PUBLICATIONS

Supplementary European Search Report, 03719904.

*Primary Examiner*—Ruth S Smith
(74) *Attorney, Agent, or Firm*—Lerner, David, Littenberg, Krumholz & Mentlik, LLP

(57) ABSTRACT

A fixture such as a local receiver coil is secured to the patient support of a magnetic resonance imaging system so that the fixture remains in position relative to the support even when the support is in a vertical orientation. The positioning apparatus is arranged to allow adjustment of the fixture position, but to limit such adjustment so that the fixture cannot interfere with the poles or other elements defining the patient-receiving gap of the magnet during movement of the patient support.

14 Claims, 19 Drawing Sheets

U.S. PATENT DOCUMENTS

| | | | |
|---|---|---|---|
| 5,680,861 A * | 10/1997 | Rohling | 600/407 |
| 5,743,264 A | 4/1998 | Bonutti | |
| 5,762,073 A | 6/1998 | Choy | |
| 5,779,637 A * | 7/1998 | Palkovich et al. | 600/415 |
| 5,926,876 A | 7/1999 | Haigh et al. | |
| 6,037,773 A | 3/2000 | Mitsumata et al. | |
| 6,141,579 A | 10/2000 | Bonutti | |
| 6,278,274 B1 | 8/2001 | Biglieri et al. | |
| 6,385,481 B2 * | 5/2002 | Nose et al. | 600/415 |
| 6,414,490 B1 | 7/2002 | Damadian et al. | |
| 6,438,402 B1 * | 8/2002 | Hashoian et al. | 600/410 |
| 7,006,860 B2 * | 2/2006 | Menon | 600/422 |
| 2001/0007054 A1 | 7/2001 | Furuta et al. | |

FOREIGN PATENT DOCUMENTS

| | | |
|---|---|---|
| DE | 93 04 457 U1 | 5/1993 |
| JP | 1305937 | 12/1989 |
| JP | 928690 | 2/1997 |
| JP | 10-57335 | 3/1998 |
| JP | 10113540 | 5/1998 |

* cited by examiner

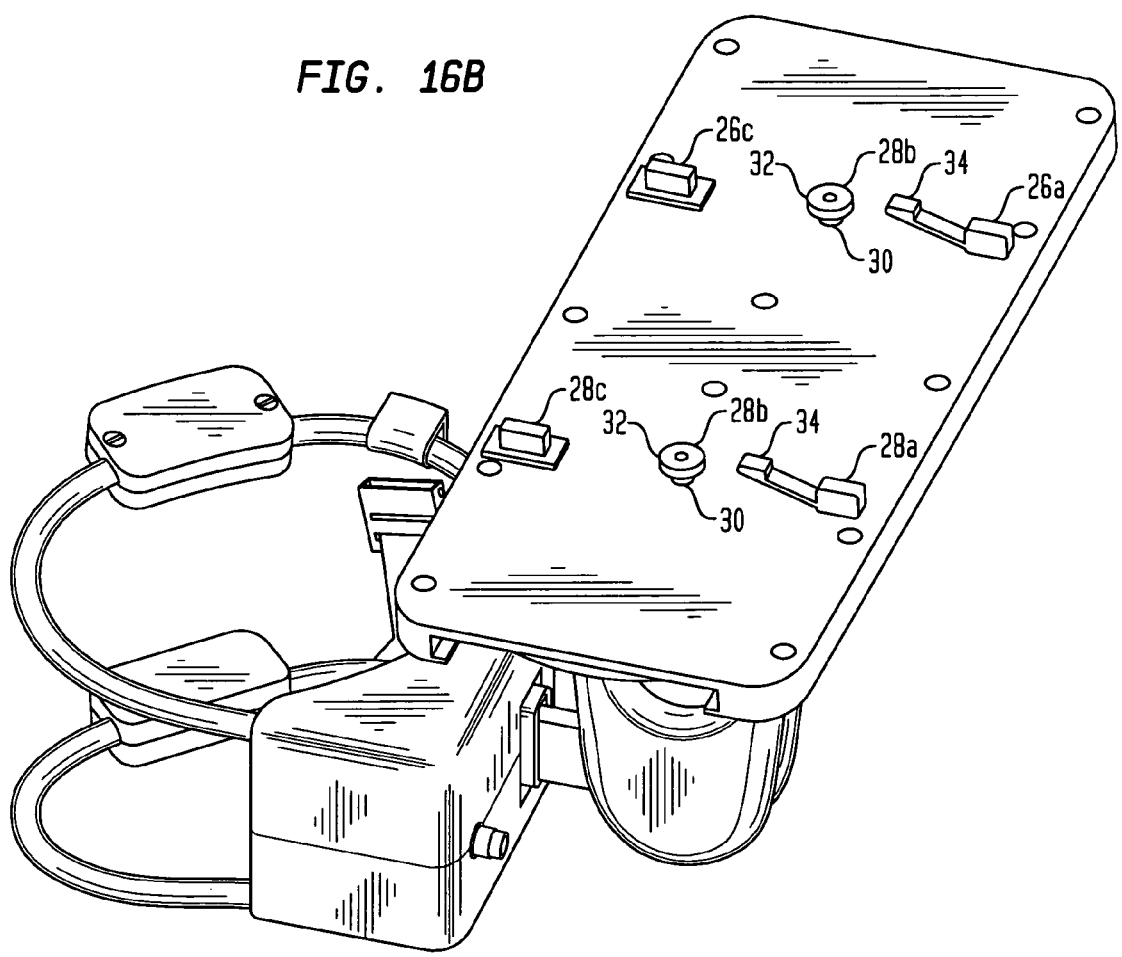

MAGNETIC RESONANCE IMAGING WITH ADJUSTABLE FIXTURE APPARATUS

CROSS-REFERENCE TO RELATED APPLICATIONS

The present application is a continuation-in-part of U.S. patent application Ser. No. 10/131,843, filed on Apr. 25, 2002 now U.S. Pat. No. 7,551,954 and entitled "Magnetic Resonance Imaging Fixture Mounting," the disclosure of which is incorporated by reference herein in its entirety.

FIELD OF INVENTION

The present invention relates to the art of magnetic resonance imaging.

BACKGROUND OF THE INVENTION

In magnetic resonance imaging ("MRI"), the body of a subject to be imaged as, for example, the body of a medical patient, is subjected to a strong static magnetic field. Radio frequency ("RF") excitation signals are applied to the subject. This causes the tissues of the subject's body to emit minuscule radio frequency signals referred to herein as "magnetic resonance signals." During the procedure, magnetic field gradients are applied so that, during different portions of the procedure, the strength of the static magnetic field varies with distance along various axes. The resulting magnetic resonance signals are spatially encoded. Thus, the magnetic resonance signals are typically generated only in a limited region as, for example, a single point, a line or a two dimensional "slice." Moreover, the signals from different portions of a line or a slice differ in frequency or phase from one another. If the procedure is repeated numerous times, it is possible, using known techniques, to recover an image data set having data elements, each representing one or more properties of the magnetic resonance signals generated within a single, small volume element or "voxel." Because properties of magnetic resonance signals vary with the composition of the material generating the signal, the signals generated by different tissues within the body will differ from one another. Thus, data elements representing voxels in different tissues will have different values. Such a data set can be used, for example, to provide a visually perceptible image such as a screen display or a printed picture showing different tissues within the body with different brightness or color.

Magnetic resonance imaging offers numerous advantages over other imaging techniques such as conventional x-ray imaging, fluoroscopy and CAT x-ray scanning. For example, MRI is capable of showing soft tissues in extraordinary detail and is capable of displaying subtle anatomical differences. Moreover, MRI does not require exposure of the subject or medical personnel to ionizing radiation.

Many conventional magnetic resonance imaging instruments require that a patient lie on a horizontal bed that is then advanced into a tubular bore within a super-conducting solenoidal magnet used to generate the static magnetic field. Other conventional MRI imaging instruments use a magnet having a ferromagnetic frame defining a patient-receiving space. Considerable effort has been devoted to design of such magnets in a manner which provides a relatively open patient-receiving space, as opposed to the claustrophobic tubular bore of the conventional solenoidal magnet. However, in these instruments as well, it has been the common practice to provide the patient on a bed which remains horizontal throughout the procedure.

It is often desirable to provide fixtures in close proximity to the patient. For example, local antennas such as small solenoidal coils can be placed around a part of the patient's body to be imaged as, for example, around the head or around a limb of the patient. These antennas can be used to transmit the RF excitation signals, to receive the magnetic resonance signals emitted by the tissue, or both. Such local antennas allow improved reception of signals from the specific region of interest within the patient's body. Other fixtures can be used for purposes such as supporting or positioning parts of the patient's body relative to a patient support such as a table or a rest for supporting the patient's head or limb. Typically, these fixtures are simply placed on the surface of the bed at the desired location for a particular patient, or are placed on the patient's body so that the fixture will be supported by the bed surface when the patient lies on the bed surface. These arrangements are satisfactory where the bed remains in a horizontal position at all times.

As described in greater detail in commonly assigned U.S. Pat. No. 6,414,490, which is a continuation of U.S. patent application Ser. No. 08/978,048, and U.S. patent application Ser. No. 09/718,946, the disclosures of which are hereby incorporated by reference herein, a magnetic resonance imaging system can be provided with a patient support, such as a table, which can extend in a generally vertical direction so that the long axis of the patient is substantially vertical. For example, the patient may be in a standing posture, with his back, side or front leaning against a generally vertical patient support. Such a support may include a footrest projecting from the table at its lower end and the patient may stand on the footrest. In other arrangements, the support includes a seat projecting from the table so that the seat is in a horizontal plane when the table surface is vertical. In particularly preferred arrangements, the patient support can move relative to the magnet. For example, the patient support may be arranged to move vertically relative to the magnet so as to elevate a portion of the patient into the patient-receiving space of the magnet. Alternatively or additionally, the patient support may be arranged to tilt through a range of orientations between a generally horizontal orientation and a generally vertical orientation.

Where the patient support table is in a generally vertical orientation during all or a portion of the procedure, fixtures positioned on the surface of the support will fall off of the support unless they are secured to the surface. Although the fixtures can be secured to the support using devices improvised for a particular application, as, for example, straps or tape, such arrangements do not offer a complete solution. Accordingly, there has been a need for improved apparatus for positioning fixtures in magnetic resonance apparatus, and for magnetic resonance apparatus incorporating such improved positioning apparatus.

SUMMARY OF THE INVENTION

One aspect of the present invention provides a magnetic resonance imaging system which includes a magnetic resonance apparatus having a structure including elements defining a patient-receiving gap and also including a patient support moveable relative to the structure through a range of support positions. The imaging system according to this aspect of the invention desirably includes a fixture positioning apparatus and a fixture. The fixture positioning apparatus is operative to secure the fixture to the patient support and to permit adjustment of the fixture relative to the patient support over a range of fixture positions. Most preferably, the range of fixture positions allowed by the fixture positioning apparatus is limited so that for any position of the fixture within the range of fixture positions, the fixture will remain clear of the elements of the structure defining the gap during movement of the patient support. A system according to this aspect of the invention provides adjustability of the fixture as required to meet patient needs, but also provides significant safety benefits. The fixture positioning apparatus prevents the technician from accidentally setting the position of the fixture relative to the support in such a manner that movement of the support will cause the fixture to crash into the gap-defining structure of the magnet.

Typically, the support has a longitudinal direction. The support may be positioned or positionable in an orientation such that the longitudinal direction of the support extends generally vertically. The range of support positions may include a range of movement in the longitudinal direction of the support. The support typically has a pair of longitudinal edges extending in the longitudinal direction. The range of fixture positions afforded by the fixture positioning apparatus most preferably includes a range of positions in a lateral direction transverse to the longitudinal direction. Desirably, the range of positions in the lateral direction is limited so that, for any position of the fixture within this range of positions in the lateral direction, the fixture is disposed entirely between the longitudinal edges of the patient support.

Preferably, the fixture positioning apparatus includes a mounting unit and one or more mount attachments that connect the mounting unit to the patient table, as well as a universal fixture-receiving unit adapted to engage the fixture. The universal fixture-receiving unit is adjustable relative to the mounting unit and preferably is adjustable relative to the mounting unit in the lateral direction, so as to provide the adjustability discussed above. In a particularly preferred arrangement, the patient support of the magnetic resonance imaging system includes one or more support tracks extending in the longitudinal direction of the support and the mount attachments include one or more guide elements arranged to engage the support tracks so that the mounting unit can be adjusted relative to the patient support in the longitudinal direction. The mount attachments desirably also include one or more arresting elements engaged with the mounting unit and with the patient support, so as to arrest the movement of the mounting unit relative to the patient support. Most preferably, the fixture-receiving unit includes a releasable connection which releasably holds the fixture to the fixture-receiving unit, so that the fixture can be removed. One or more additional fixtures can be provided, and the releasable connection of the fixture-receiving unit is arranged to engage any of the fixtures. Thus, the fixtures are interchangeable. The additional fixtures may be of different configurations to meet different patient needs.

A further aspect of the invention provides fixture-positioning apparatus for use in a magnetic resonance imaging system as discussed above. The fixture-positioning apparatus according to this aspect of the invention desirably includes a mounting unit and one or more mount attachments adapted to connect the mounting unit to a patient support of a magnetic resonance apparatus. The fixture-positioning apparatus further includes a fixture-receiving unit adapted to hold a fixture. The fixture-receiving unit and the mounting unit desirably are engagable with one another, so that the fixture-receiving unit can be adjusted over a range of positions relative to the mounting unit. This allows adjustment of the fixture held in the fixture-receiving unit relative to the patient support, as discussed above. The mounting unit desirably defines a track direction, and the mount attachments are arranged to secure the mounting unit to the patient support, so that the track direction is transverse to the direction of elongation of the support. The fixture-receiving unit desirably is slideable in the track direction relative to the mounting unit when the fixture-receiving unit is engaged with the mounting unit.

The fixture-receiving unit and mounting unit desirably have stops engagable with one another, so as to limit the position of the fixture-receiving unit in the track direction. The fixture-receiving unit may be adapted to hold a fixture in the form of a coil so that the axis of the coil extends transverse to the track direction and, hence, extends in the longitudinal direction of the patient support when the unit is assembled with the patient support. Preferably, the fixture-receiving unit defines a cradle having an axis disposed transverse to the track direction and also includes one or more releasable latches arranged to engage corresponding features on coils or other fixtures. In a particularly preferred arrangement, detents are provided for holding the fixture-receiving unit at predetermined locations within its range of motion in the track direction.

The preferred positioning apparatus and magnetic resonance systems in accordance with these aspects of the present invention provide secure attachment of fixtures to the patient support and are operable with the support in a vertical orientation, as well as other orientations such as a horizontal orientation, a Trendelenburg orientation in which the head end of the fixture, with the patient's head is lower than the foot end, and intermediate orientations. The most preferred structures in accordance with these aspects of the invention provide the versatility needed to accommodate a wide range of procedures using various fixtures disposed in various locations, and also provide for quick changes of fixtures and positions. Moreover, the preferred apparatus and systems according to these aspects of the invention provide significant safety benefits.

A further aspect of the invention provides methods of operating a magnetic resonance system. A method according to this aspect of the invention desirably includes the steps of positioning a first fixture on a patient support of a magnetic resonance apparatus using a fixture positioning apparatus and adjusting the position of the fixture relative to the patient support by adjusting the fixture positioning apparatus. Preferably, the method also includes the step of moving the patient support within a range of support positions between a pair of magnet elements defining a gap. Most desirably, the fixture positioning apparatus limiting the position of the fixture after completion of the adjusting step so that the fixture does not interfere with the pair of magnet elements during the step of moving the patient support. Methods according to this aspect of the invention may include the further step of disengaging the fixture from the fixture positioning apparatus and replacing the fixture with another fixture. The adjusting and moving steps can be repeated using the new fixture.

Another aspect of the present invention is a device for use in magnetic resonance imaging. The device comprises a base member and first and second antenna loop portions, which are threaded through the base member. The base member is orientable relative to a patient's anatomy such that the first antenna loop portion is adjacent to an anterior surface of the patient and said second loop portion is adjacent to a posterior surface of the patent. Devices implemented in accordance with this aspect of the invention advantageously improve the capability of magnetic resonance imaging by making it possible to capture magnetic resonance signals emanating from either or both the anterior and posterior surfaces of a patient's anatomy.

In an embodiment in accordance with this aspect of the present invention, the anterior and posterior surfaces comprise the front and rear surfaces of the patient's head.

In another embodiment, the anterior and posterior surfaces comprise a portion of the front and rear surfaces of the patient's torso.

In yet a further embodiment, the anterior and posterior surfaces comprise the front and rear surfaces of a patient's extremities.

An additional aspect of the present invention is a fixture comprising a base plate and an antenna portion. The antenna portion includes a base member that is pivotably mounted to the base plate and at least one coil forming a loop. The coil loop is threaded through the base member with the base member serving to hold the coil loop in place. This fixture is particularly advantageous for imaging the shoulder area of a human patient.

Further in accordance with this aspect of the invention, the base member is pivotably mounted to the base plate by a pair of saddle shape members and an arm having a donut shaped end. The donut shaped end of the arm is mounted between the saddle shape members by a locking mechanism. The locking mechanism advantageously allows a technician to manually adjust the position of coils to snuggly fit around the patient's shoulder.

In accordance with another aspect of the present invention a system for magnetic resonance imaging is disclosed. The system comprises a mounting apparatus and a fixture usable in conjunction with the magnetic resonance apparatus. The mounting apparatus is operative to secure the fixture to the patient support and to permit adjustment of the position of the fixture relative to the patient support. The fixture includes a base plate and an antenna assembly having a base member pivotably mounted to the base plate and includes at least one coil antenna in the shape of a loop that is threaded through the base member.

In accordance with a further aspect of the present invention, a method for operating a magnetic resonance apparatus is provided. The method comprises positioning a fixture on a patient support of a magnetic resonance apparatus using a mounting device and positioning a patient on the patient support such that the shoulder region of the patient is saddled by the fixture. The patient's shoulder is then imaged by eliciting magnetic resonance signals from the tissues in the shoulder region.

An additional aspect of the present invention is a system comprising a magnetic resonance imaging apparatus having a structure including opposed elements defining a patient receiving space therebetween, a magnet axis extending substantially horizontally and a patient support. The patient support is capable of supporting a patient in a substantially upright position and is located within the structure. The system further includes a support arm mounted to the patient support such that the support arm projects from the patient support. The system advantageously allows a patient to be imaged in a variety of positions, including the standing or sitting position while the support arm holds a device used as part of the imaging process.

In a preferred embodiment the support arm is adaptable to receive a plurality of devices usable in the imaging process including coil antenna assemblies, monitors associated with monitoring various aspects of a patient's vital signs, and other devices useful in enhancing diagnosis.

BRIEF DESCRIPTION OF THE DRAWINGS

FIG. 16B is a rear perspective view of FIG. 16A.

DETAILED DESCRIPTION OF THE PREFERRED EMBODIMENTS

Figure 1:
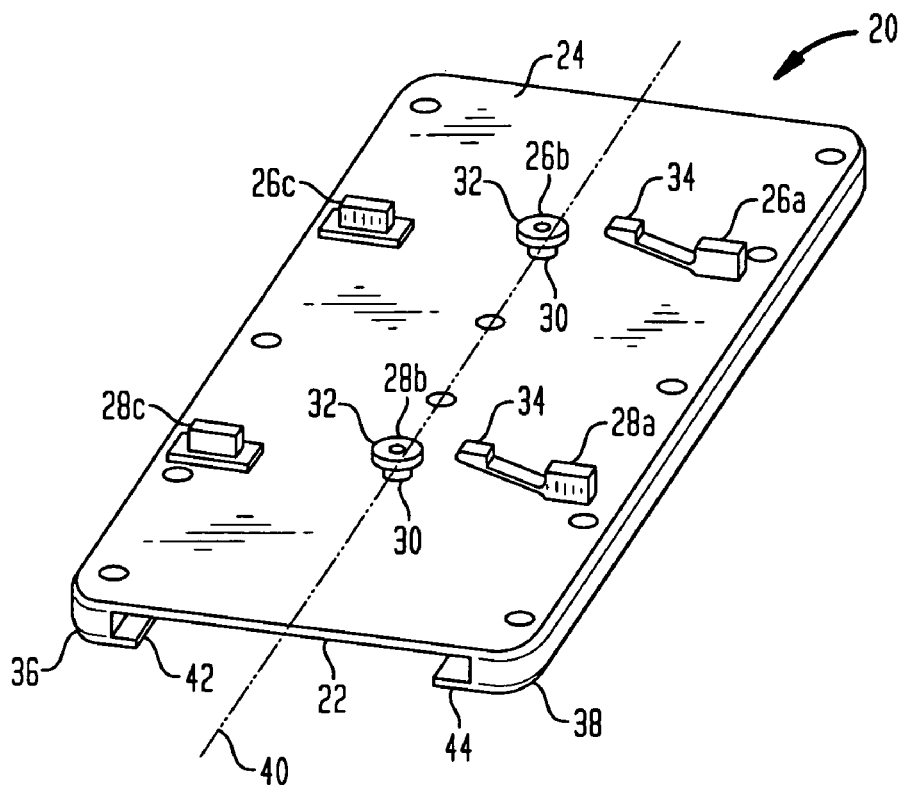
FIG. 1 is a diagrammatic perspective view of a component of a fixture-positioning apparatus according to one embodiment of the invention.
Figure 2:
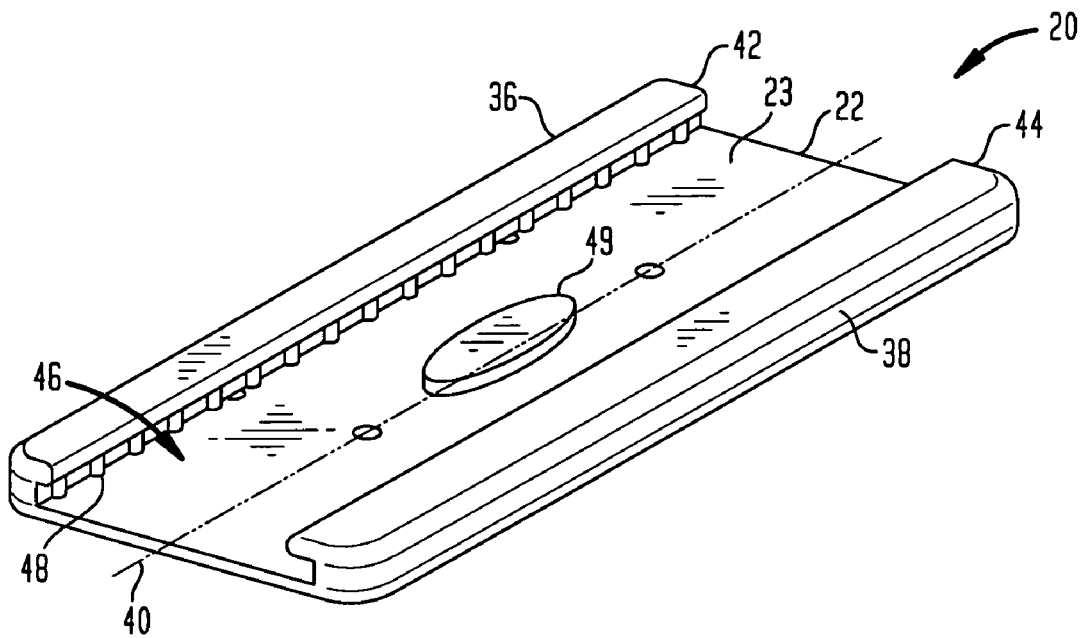
FIG. 2 is a perspective view, from an opposite perspective, of the components shown in FIG. 1.

A positioning apparatus in accordance with one embodiment of the invention includes a mounting unit 20 (FIGS. 1 and 2). The mounting unit includes a lower plate 22 having a bottom surface 24. A first set of guide elements 26a-26c projects from the bottom surface in a row extending across the bottom plate. A second set of guide elements 28a-28c also projects from the bottom surface. The guide elements of the second set are arranged in a row parallel to the row formed by the first set of guide elements 26. The first set of guide elements includes a center guide element 26b in the form of a shoulder bolt having a relatively small diameter neck portion 30 adjacent the bottom face 24 of the bottom plate and having a relatively large diameter head 32 spaced away from the bottom face 24. The remaining guide units 26a and 26c of the first set are generally rectangular, solid elements. The guide elements 28 of the second set include end elements 28a and 28c, similar to the end elements 26a and 26c of the first set, and a center guide element 28b, similar to those of center guide element 26b. A pair of resilient arresting elements 34 is formed integrally with the end guide elements 26a and 28a. These end elements are flexible in directions towards and away from the bottom plate 22, i.e., upwardly and downwardly as seen in FIG. 1.

As depicted in FIG. 2, mounting unit 20 is inverted relative to the position shown in FIG. 1, so that the top surface 23 of the bottom plate 22 is facing upwardly in FIG. 2. The mounting unit has a pair of side rails 36 and 38 projecting upwardly from the top surface 23. The side rails extend generally in a track direction, i.e., the direction indicated by axis 40. Rails 36 and 38 (FIG. 2) extend generally along opposite edges of bottom plate 22. The first rail 36 has a flange 42 projecting inwardly from the upper end of the rail, i.e., the edge of the rail remote from bottom plate 22. The second rail 38 has a similar flange 44 projecting inwardly towards rail 36. The rails, flanges and bottom plate 22 cooperatively define a track in the form of a generally T-shaped slot 46 extending in track direction 40. The first rail 36 is provided with a series of detent bumps 48 disposed between flange 42 and bottom plate 22. Detent bumps 48 are disposed at regular intervals as, for example, about 2.5 cm (one inch) between detent bumps. A stop 49 projects upwardly from the top surface 23 of bottom plate 22 within slot 46. As seen in FIG. 1, the first rows of guide elements 26 extend transverse to the track direction 40 and the second row of guide elements 28 also extends transverse to the track direction.

A universal fixture-receiving unit 50 (FIGS. 3 and 4) includes a base plate 52 having a pair of oppositely directed long edges 54 and 56 and an elongated central slot 58. A pair of end risers 60 and 62 project upwardly from the base plate 52 at opposite ends thereof. End riser 62 has a generally rectangular slot 64 in its inner face, the face of riser 62 facing toward the opposite riser 60. Slot 64 is open to the upper end of riser 62 facing away from base plate 52.

A latch 66 projects into slot 64. The latch has a gradually sloping face facing toward the open end of slot 64. Latch 66 is carried on a resilient spring arm 68, seen in broken lines in FIG. 3, disposed within a cavity in end unit 64. The cavity is covered by a plate 70. A release button 72 is exposed at an edge of end unit 62. Button 72 is connected through a rod 74 to spring arm 68, so that when button 72 is depressed manually, latch 66 is moved out of slot 64. The opposite end unit 60 has a slot 76 equipped with a similar latch 77, resilient arm 79, and a similar release button 78.

A pair of plates 80 and 82 projects upwardly from the base plate 52 and extend between end risers 60 and 62. Plates 80 and 82 are spaced inwardly from edges 54 and 56 of the base plate 52. Thus, a region of the base plate between first edge 54 and plate 80 defines a first lip 84, whereas another portion of the base plate between plate 82 and second edge 56 defines another lip 86. Plates 80 and 82 have semicircular indentations 88 and 90 in their top edges so that these plates cooperatively define a cradle in the form of a sector of a circular cylinder having a cradle axis 92. The cradle axis extends transverse to the edges 54 and 56 of the base plate and, hence, transverse to the direction of elongation of the base plate.

Figure 4:
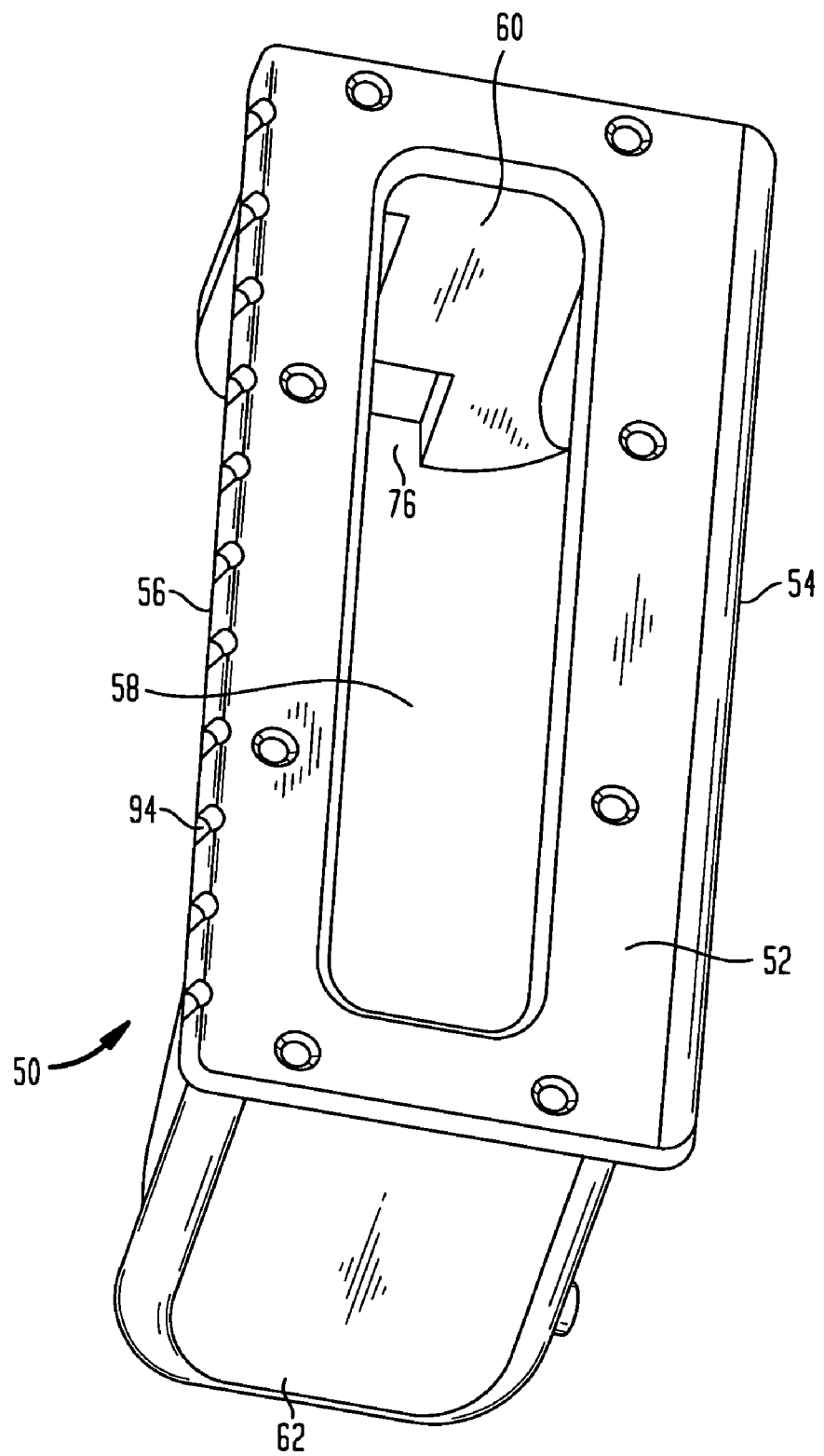
FIG. 4 is a diagrammatic perspective view, from an opposite perspective, of the component shown in FIG. 3.

As best seen in FIG. 4, the second edge 56 of base plate 54 is provided with a series of detent notches 94 spaced apart from one another at regular intervals along the length of the edge. The spacings between notches 94 correspond to the spacings between detent bumps 48 of the mounting unit (FIG. 2).

Figure 5:
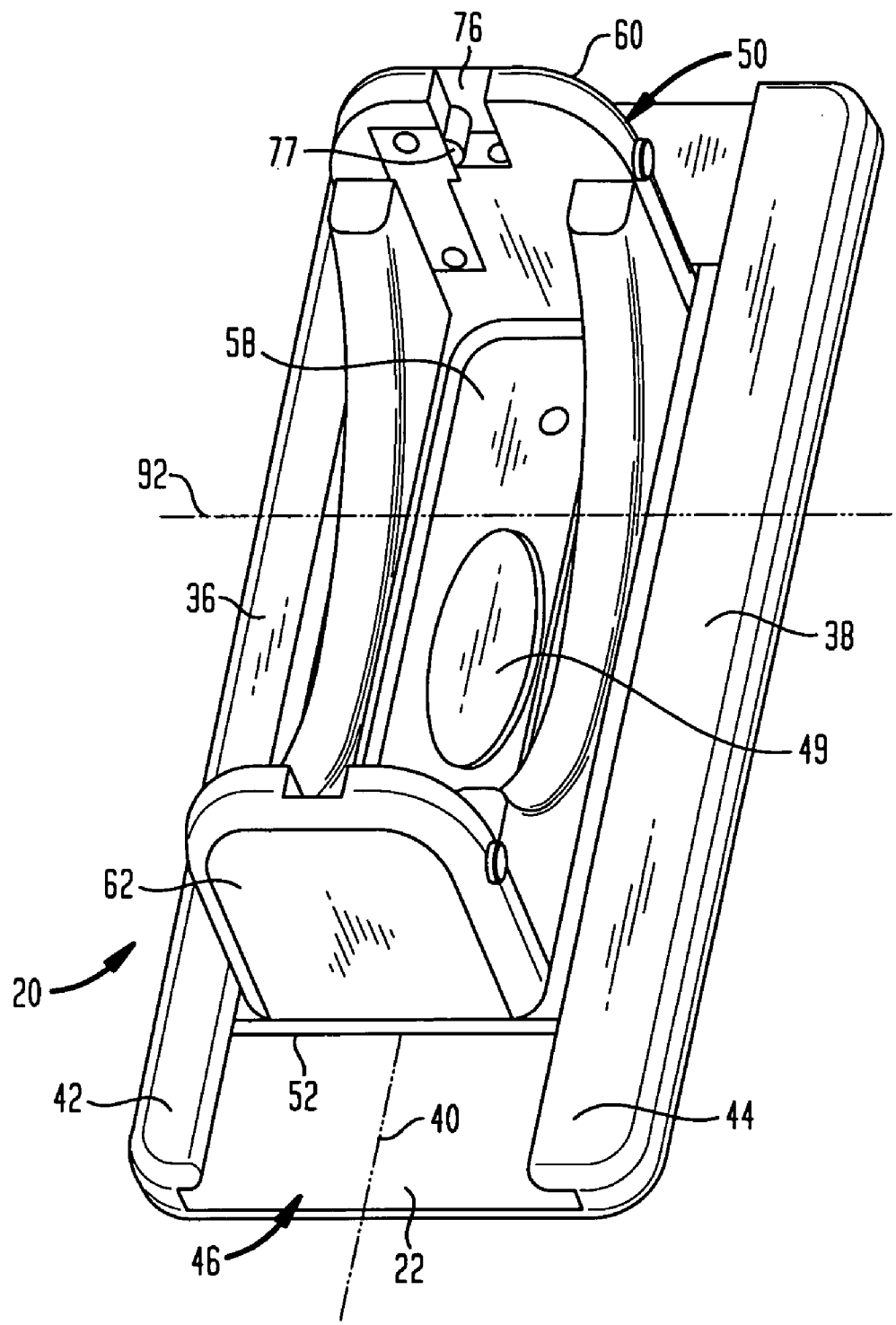
FIG. 5 is a diagrammatic perspective view of the fixture-positioning apparatus incorporating the components of FIGS. 1-4.

As seen in FIG. 5, universal fixture-receiving unit 50 is assembled with mounting unit 20 so that the base plate 52 of the fixture-receiving unit is disposed in the slot 46 of the mounting unit. Thus, the lips at the edges of the base plate are disposed beneath the flanges 42 and 44 of the mounting unit. The lengthwise direction of base plate 52 and, hence, edges 54 and 56 (FIGS. 3 and 4) extend in the track direction 40 defined by the mounting unit. The cradle axis 92 of the fixture-receiving unit is perpendicular to the track direction 40. The second edge 56 (FIG. 4) of the base plate on the fixture-receiving unit is disposed beneath flange 42 of the first rail 36 on the mounting unit, whereas the first edge 54 of the fixture-receiving unit (FIG. 4) is disposed beneath flange 44 of the second rail 38. In the position illustrated in FIG. 5, some of the detent notches 94 (FIG. 4) on the base plate 52 are engaged with some of the detent bumps 48 (FIG. 2) on first rail 36. However, the distance between edges 56 and 54 of the fixture-receiving base plate is slightly less than the distance between rails 36 and 38, so that the fixture-receiving unit can be shifted slightly in the direction towards rail 38 and transverse to track direction 40 to disengage the detent bumps and detent notches. In this shifted condition, the fixture-receiving unit 50 is slideable along track or slot 46 in track direction 40 relative to the mounting unit 20.

Stop 49 of the mounting unit is disposed within slot 58 of the base plate. The stop limits the range of travel of the fixture-receiving unit relative to the mounting unit. At one extreme, the first end riser 60 of the fixture-receiving unit is aligned with the end of mounting unit 20 towards the top of the drawing in FIG. 5. At the opposite extreme of the range of motion, the other end riser 62 is aligned with the opposite end of mounting unit 20. Thus, at all positions within the range of motion allowed by stop 49 and slot 58, the fixture-receiving unit 50 is disposed entirely within the length of mounting unit 20 in the track direction 20.

Figure 6:
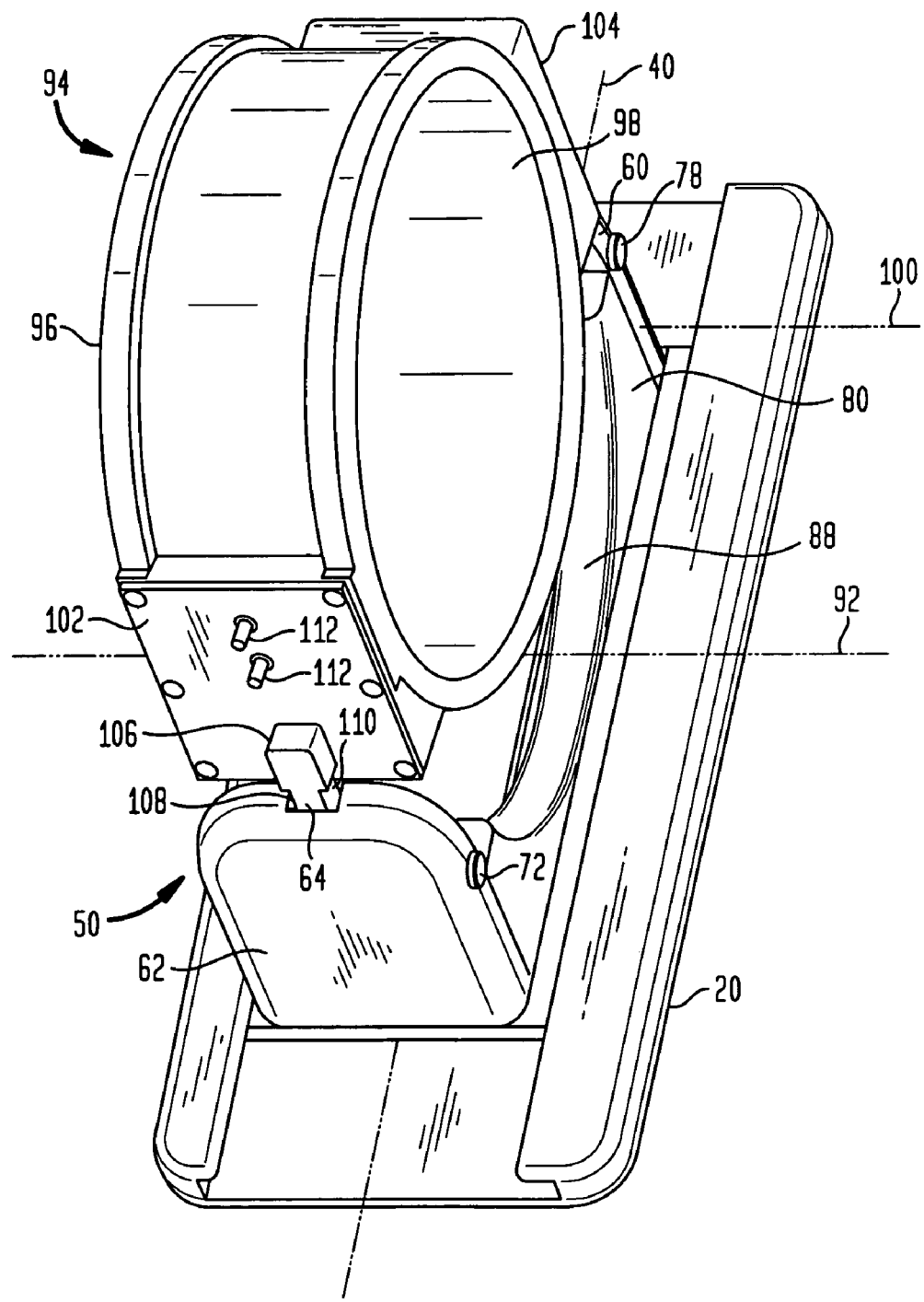
FIG. 6 is a diagrammatic perspective view of the apparatus shown in FIG. 5 in conjunction with a fixture.

As shown in FIG. 6, the fixture-positioning assembly of FIGS. 1-5 can be used with a fixture such as a local RF coil 94. The coil includes generally conventional windings enclosed in a toroidal housing 96 having an interior bore 98. The coil defines a coil axis 100 extending through the center of the bore. Coil 94 also has a pair of mounting pads 102 and 104. Pad 102 defines a flat surface having a generally rectangular block 106 projecting from such surface. Block 106 has notches 108 and 110 extending into it from opposite sides. Block 106 is elongated in a direction transverse to the coil axis 100. Pad 104 defines a similar surface and block (not shown). Pad 102 has a pair of electrical contacts 112 projecting from its surface. The coil unit may also include other components (not shown) commonly used in conjunction with a receiving coil as, for example, a tuning capacitor or a preamplifier, which may be disposed within one or both of the pads. Electrical connectors 112 are connected to the windings of the coil and to other electrical components. In use, these connectors are connected by a conventional cable (not shown) to the RF transmitting and/or receiving devices of the magnetic resonance apparatus. In other embodiments, connectors 112 can be replaced by a cable permanently connected to the coil.

The coil is engaged with the fixture-receiving unit 50 by positioning the coil as shown in FIG. 6 and advancing the coil downwardly towards the fixture-receiving unit, so that block 106 enters into the slot 64 in end riser 62 and the corresponding block on pad 104 enters into the slot 76 (FIG. 5) of end unit 60. As the blocks enter into the slots, they force the catches 66 and 77 (FIGS. 3 and 5) out of the slots against the bias of the spring arms. The catches have sloping surfaces facing towards the open ends of the slots for this purpose. When the coil is fully seated and the blocks are bottomed in the slots of the end units, the latch 66 within slot 64 engages in one of the slots 108 or 110 on block 106, and the corresponding latch 77 of end riser 60 engages the block on pad 104 in a similar fashion. Thus, the coil is firmly held in the end units. The toroidal housing 96 of the coil is received in the U-shaped cradle defined by the walls 88 and 90 of the fixture-receiving unit. In this condition, the coil axis 100 extends parallel to the cradle axis 92 and, hence, extends transverse to the track direction 40 of the mounting unit.

The coil is encompassed within the length of the fixture-receiving unit 50 in the track direction 40. That is, the coil is disposed between end risers 60 and 62. As pointed out above, the range of motion of the fixture-receiving unit relative to the mounting unit is limited so that the fixture-receiving unit remains entirely within the length of mounting unit 20 in the track direction. Therefore, the coil also will remain entirely within the length of the mounting unit 20.

Figure 7:
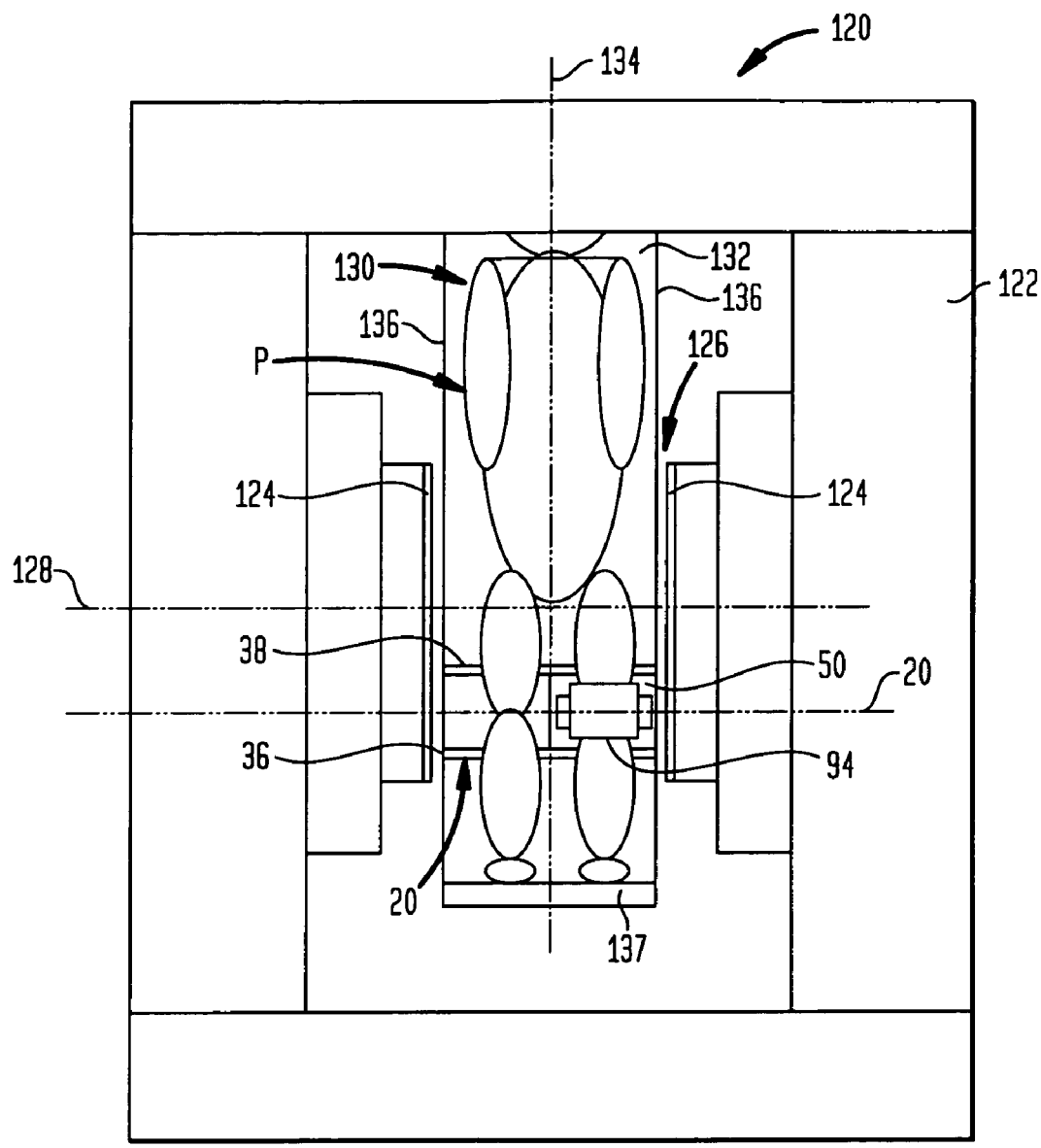
FIG. 7 is a diagrammatic elevational view of a magnetic resonance imaging system according to one embodiment of the invention incorporating the fixture-positioning apparatus of FIGS. 1-6.

The fixture-positioning apparatus is employed in conjunction with a magnetic resonance imaging apparatus 120 (FIG. 7). The particular apparatus illustrated is generally in accordance with the disclosure of the aforementioned copending, commonly assigned U.S. patent applications. It includes a magnet 122 which has a pair of opposed elements 124 defining a patient-receiving gap 126 between them. In the particular magnet illustrated, the opposed elements are pole faces, but in other types of magnets opposed elements may be elements of superconducting or resistive electromagnet coils or other structures. The magnet is arranged to provide a magnetic field surrounding a magnet axis 128 within patient-receiving gap 126. The magnet axis extends substantially horizontally. The magnetic resonance imaging apparatus further includes a patient handling apparatus incorporating an elongated patient support 130 having a patient-receiving surface 132 and a longitudinal direction 134. A footrest 137 projects from surface 132 at one end. The patient-receiving surface is bounded by a pair of longitudinal edges 136. In the condition illustrated in FIGS. 7 and 8, the patient-receiving surface lies in a generally vertical plane and the longitudinal direction 134 of the patient support extends generally vertically, typically within about 15° of vertical. The widthwise or lateral dimension of the patient-receiving table transverse to longitudinal direction 134 is just slightly less than the dimension of gap 126 between opposed elements 124 of the magnet. The lateral dimension of the patient support is parallel to magnet axis 128.

Patient support 130 is associated with a carriage 138 and drive at 140 arranged to move the patient support 130 in its direction of elongation and to tilt the support between the vertical condition illustrated and a horizontal condition (not shown) in which the patient-receiving surface 132 and longitudinal direction 134 are generally horizontal.

Figure 9:
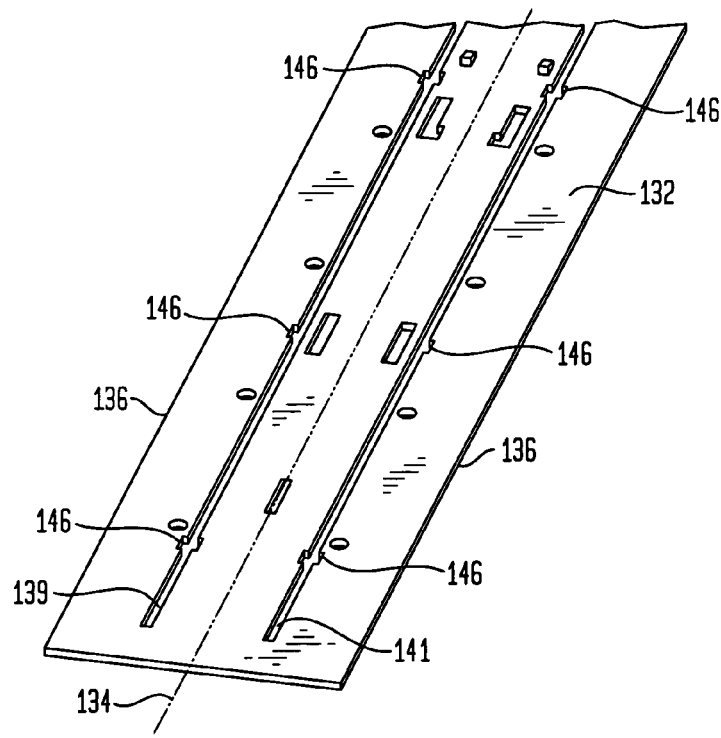
FIGS. 9 and 10 are fragmentary perspective views of a patient support incorporated in the apparatus of FIGS. 7 and 8.
Figure 10:
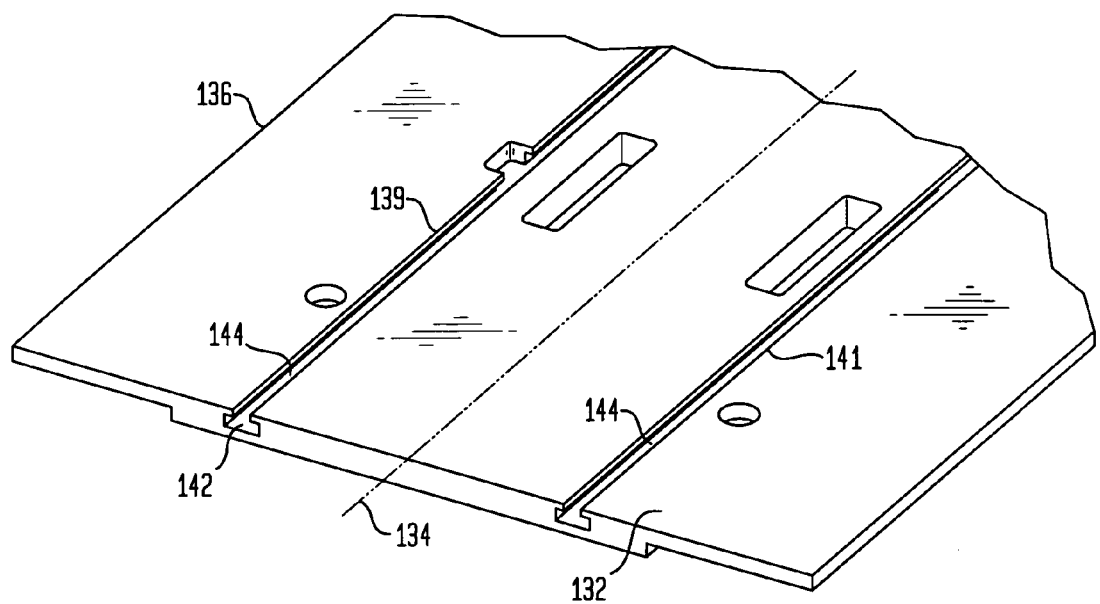

As seen in greater detail in FIGS. 9 and 10, the patient-receiving surface 132 has a pair of slots 139 and 141 extending parallel to one another and extending in the longitudinal direction 134 of the support. As best seen in FIG. 10, slots 139 and 141 are generally T-shaped in cross-section. Thus, each slot has a narrow top portion 144 where the slot opens to the surface 132 remote from the opening of the slot. Pockets 146 are provided in pairs (FIG. 9) along the lengths of the slots. These pockets are wider than the narrow portions 144 of the slots.

The fixture-positioning apparatus, with or without a fixture thereon, can be engaged with the patient support 130 of the MRI apparatus by placing the positioning apparatus against the patient-receiving surface 132 so that the bottom surface 24 of mounting unit 20 (FIG. 1) confronts surface 132, and so that one row of guides 26 is aligned with slot 138 and the other row of guides 28 is aligned with the slot 140. The center guides 26b and 28b are aligned with one set of pockets 146. In this condition, the heads 32 of the center guides (FIG. 1) enter into the pockets, whereas the end guides 26a, 26c, 28a and 28c are engaged in the narrow portions 144 of the slots. The apparatus is then shifted in the longitudinal direction of the table until it is at the desired location relative to the table. The heads 32 of the center guides are trapped in the wide portions 142 of the slots. Arresting catches 34 (FIG. 1) on the mounting unit frictionally engage the bottoms of slots 138 and 140 and, hence, hold the mounting unit in position along the length of the support. The mounting unit 20 desirably is installed on the patient support 130 so that the first rail 36 bearing the detent bumps 48 (FIG. 2) faces towards the footrest 137 at the foot end of the patient support. This assures that, when the patient support is in the vertical orientation as shown, gravity forces the fixture-positioning unit and fixture downwardly, towards the first rail and helps hold the detent bumps 48 in engagement with the detent notches 94 (FIG. 4) on the edge of the fixture-positioning unit base plate. Typically, the fixture-positioning apparatus is secured to the patient support before engaging the fixture with the fixture-positioning apparatus.

In the assembled condition, the mounting unit and, hence, the rest of the fixture-positioning assembly and the fixture are held firmly to the patient support. Also, in this condition, the mounting unit is constrained against movement relative to the table in the lateral direction, transverse to the longitudinal direction 134 of the patient support. The track direction 40 of the guide unit (FIGS. 2, 5 and 6) is transverse to the longitudinal direction of the table. The length of the guide unit in the track direction is less than or equal to the width of the patient support, i.e., slightly less than the distance between the longitudinal edges 136 of the patient support. Thus, the entire positioning assembly and fixture are contained within the width of the patient support. Fixture-positioning unit 50 and fixture 94 are also contained within the width of the patient support. As discussed above, the fixture-positioning unit and fixture can be moved in the track direction 20 over a limited range of motion. However, in any position of the fixture-positioning unit relative to the mounting unit, the fixture-positioning unit 50 and fixture 94 are entirely contained within the length of the mounting unit in the track direction 20 and, hence, entirely contained within the width of the patient support.

The technician can position the fixture readily, without the use of tools. The fixture can be repositioned as desired for a particular procedure. For example, as seen in FIG. 7, the fixture 94 is positioned to encompass the right knee of a patient P, and the patient's knee extends through the bore of the coil housing 94. The patient's left leg extends across mounting unit 20. However, because mounting unit 20 has a low profile and protrudes from the surface 132 of the patient support by only a small distance as, for example, about one inch, the mounting unit does not cause any substantial discomfort or impede positioning of the patient's left leg. Pillows or padding may be disposed between the patient and mounting unit 20.

Because the fixture or coil 94, and the entire fixture-positioning apparatus, including mounting unit 20 and fixture-positioning unit 50, are entirely disposed within the width of the patient support 130 between longitudinal edges 136, these components do not impede movement of the patient support 130. These components cannot collide with the gap-defining elements 124 of the magnet.

Figure 11:
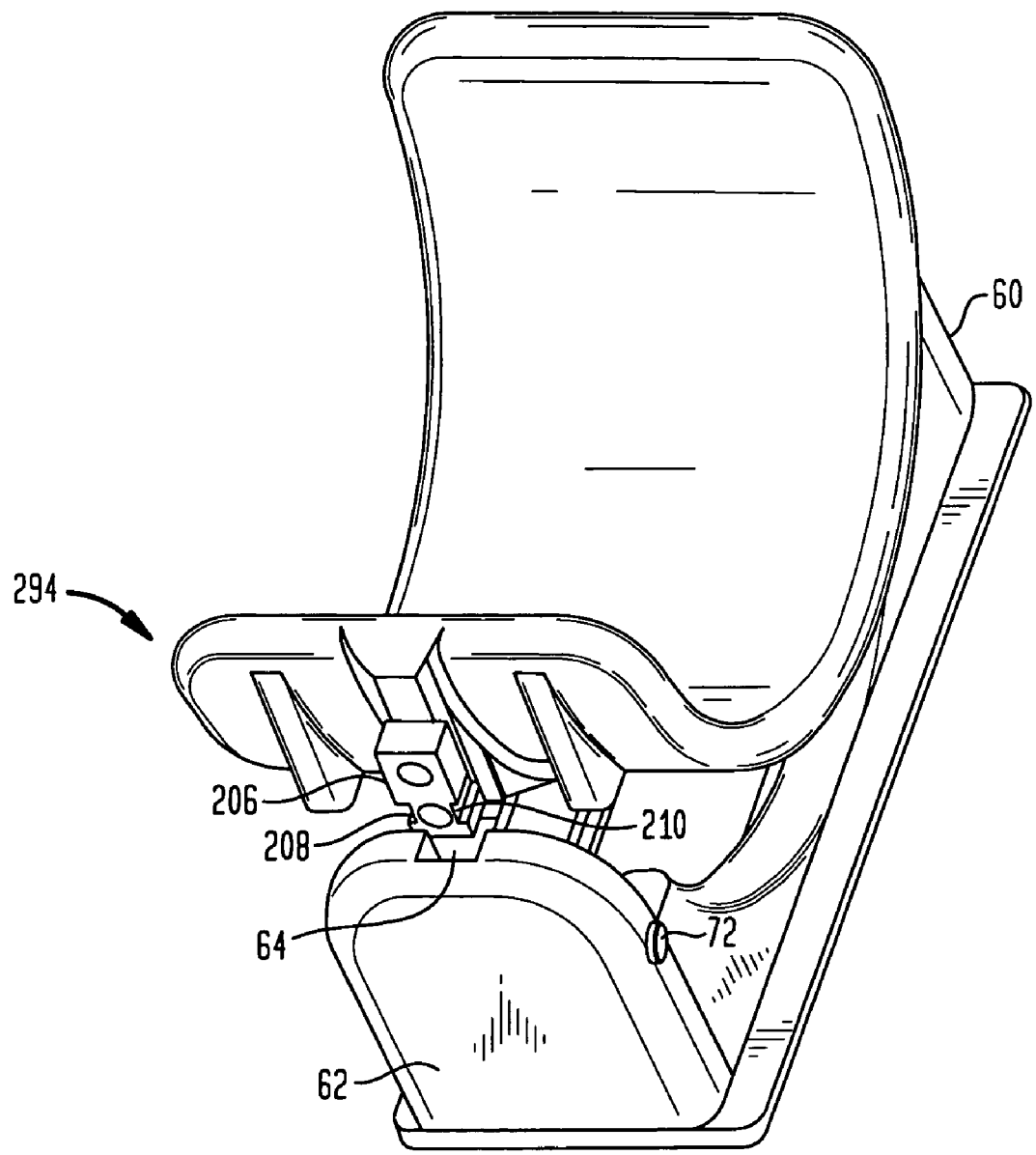
FIG. 11 is a diagrammatic perspective view depicting a part of the apparatus of FIGS. 1-5 in conjunction with a further fixture.

The same fixture-positioning apparatus, including mounting unit 20 and fixture-receiving unit 50, can be used to mount other fixtures. For example, as seen in FIG. 11, a generally U-shaped headrest 294 can be mounted in the fixture-positioning apparatus in place of coil 94. Headrest 294 is equipped with a block 206 identical to block 106 (FIG. 6) and with a corresponding block (not shown) on the opposite side of the headrest. The configuration of the blocks on the headrest is identical to the configuration of the blocks on coil 94. Thus, the headrest can be engaged in the mounting slot 64 of end unit 62 and in the corresponding mounting slot of end unit 60 in the same way as the coil 94. Still other fixtures can be provided with the same configuration of blocks, so that all of these fixtures can be used interchangeably. A fixture can be disengaged from the fixture-positioning assembly by depressing the release buttons 72 and 78 (FIGS. 3 and 6) to retract latches 66 and 77 out of engagement with the slots in the mounting blocks of the fixture and lifting the fixture out of the slots. This can be done while the fixture-positioning apparatus remains in place on the patient support.

The components of the fixture-positioning assembly desirably are formed from non-metallic materials as, for example, polymers such as acetal, commonly sold under the trademark Delrin, polyvinyl chloride, polycarbonate, commonly sold under the trademark Lexan, acrylic, commonly sold under the designation Plexiglass, or fiber-reinforced polymers such as that sold under the designation G10, or wood.

Figure 8:
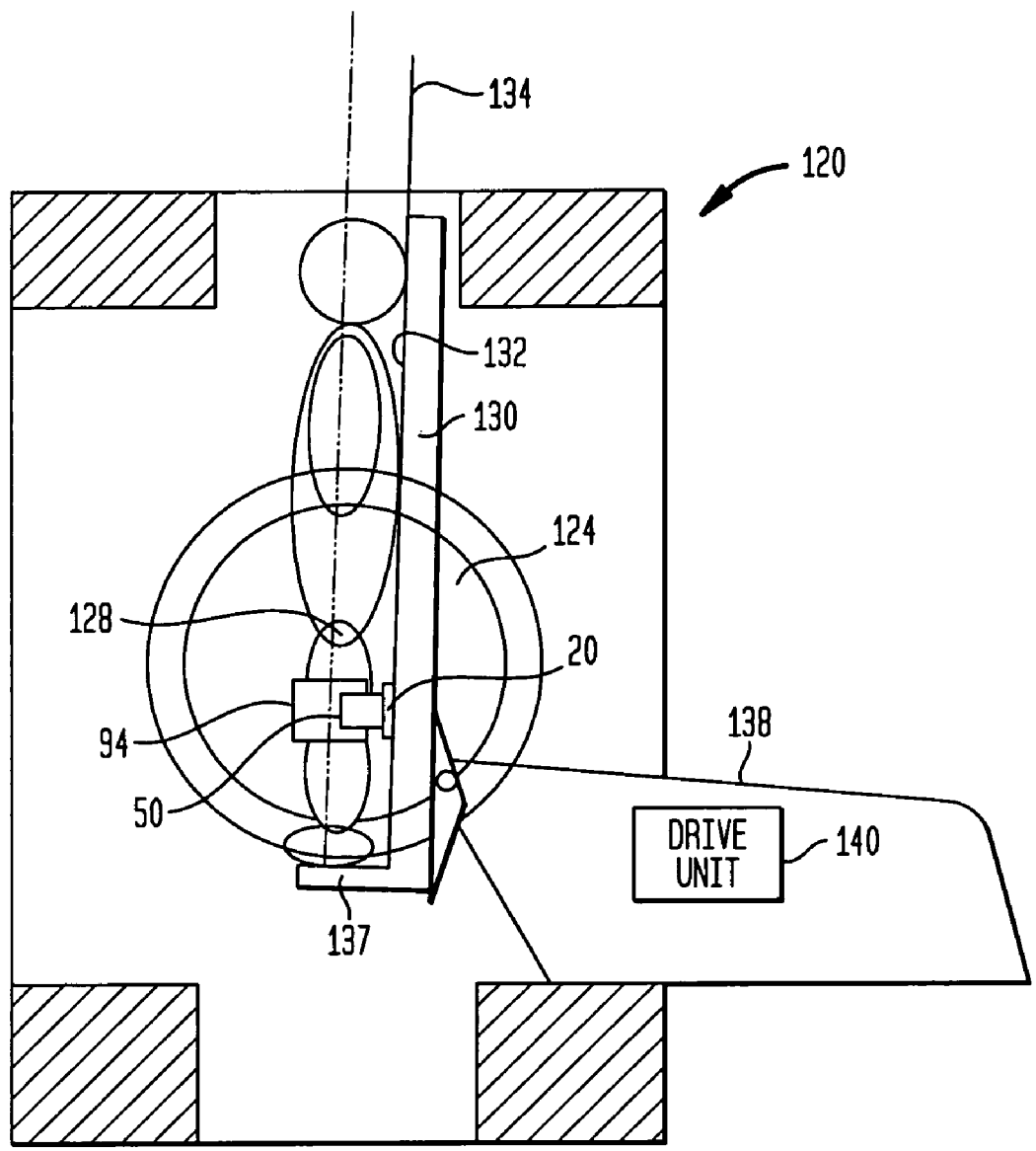
FIG. 8 is a diagrammatic sectional view of the apparatus shown in FIG. 7.

Numerous variations and combinations of the features discussed above can be utilized without departing from the present invention. For example, although only one fixture-positioning assembly is illustrated in FIGS. 7 and 8, the patient support can be equipped with as many fixture-positioning assemblies and fixtures as desired. Also, the frictional arresting elements 34 (FIG. 1) used to hold mounting unit 20 against movement in the longitudinal direction of the patient support can be replaced by other locking mechanisms. For example, the mounting unit can be provided with a manually operable cam, screw or other mechanism for forcibly engaging a locking element against the patient support. Alternatively, the patient support can be provided with a series of holes arranged in a row in the longitudinal direction of the support, and mounting unit 20 can be provided with a locking pin that can be selectively engaged in any one of these holes to hold the mounting unit in position. Also, other fastening devices such as bolts, hook and loop fasteners such as those sold under the trademark VELCRO, or suction cups can be employed. In a further variant, the patient support can be provided with an element adjustable in the longitudinal direction of the patient support, and the fixture positioning apparatus can be secured to this adjustable element. For example, the adjustable element may be a belt, chain or cable having a run extending in the longitudinal direction of the patient support, and the patient support may include an appropriate mechanism such as a set of drums or sprockets for controllably moving the belt, chain or cable. In this arrangement, the position of the fixture positioning apparatus in the longitudinal direction of the patient support can be adjusted by moving the adjustable element.

As discussed above, gravity tends to hold the detent bumps 48 (FIG. 2) in engagement with the detent notches 94 (FIG. 4) while the assembly is mounted on the patient support which is in a vertical orientation. To assure that the bumps and notches remain engaged when the patient support is tilted to a horizontal orientation, a spring (not shown) may be provided on the second rail 38 or on the edge 54 of base plate 52 so as to urge the base plate towards the first rail 36 and detent bumps 48. Other types of detent mechanisms can be substituted for the bumps and notches discussed above. For example, the track can be dimensioned so as to prevent movement of the base plate transverse to the track direction. One or more spring-loaded detent elements can be mounted on first rail 36 so that these elements engage in detent notches 94. Alternatively, the mounting unit 20 can be provided with a series of holes arranged in a row along the track direction 40 and the fixture-receiving unit 50 can be provided with a manually operable locking pin, which can be engaged in any of these holes. The configuration of the track on the mounting unit can be varied. For example, the mounting unit can have a track element of square, dovetail or other configuration projecting upwardly from the surface of bottom plate 22, and the fixture-receiving unit 50 can be provided with a slot engagable on this track element.

In a further variant, the detent arrangement may be omitted entirely and an appropriate brake or grasp mechanism may be provided on the fixture-positioning unit or on the mounting unit for locking the fixture-receiving unit to the mounting unit at any position along the track. Also, a screw may be provided on one unit and engaged with the mating unit so that the position of the fixture-receiving unit in the track direction can be adjusted by turning the screw. In all of these variants, it is desirable to provide stops to limit the range of motion of the fixture-receiving unit relative to the mounting unit as described above.

The elements which mount the fixture to the fixture-receiving unit, such as the blocks 106 (FIG. 6) and the mating slots 64 on the fixture-receiving unit, can be replaced by other types of inter-engagable elements. For example, the fixtures can be provided with pins and the fixture-receiving unit can have mating holes, or vice-versa. Here again, however, the mating elements on each fixture should be identical to those on other fixtures, so that the fixtures can be used interchangeably. The mounting unit or the fixture-receiving unit can be configured to provide additional degrees of freedom in positioning of the fixture relative to the patient support. For example, the end risers 62 and 60 of the fixture-receiving unit can be arranged to tilt relative to the base plate 54 and, thus, allow the fixture to tilt relative to the patient-receiving table. Also, the end risers may be provided with mechanisms for elevating the fixture away from the base plate 54 or lowering the fixture toward the base plate.

In the embodiments discussed above with reference to FIGS. 1-10, the fixture-receiving unit is arranged to hold a coil so that the coil axis extends perpendicular to the track axis and thus extends parallel to the longitudinal direction 134 of the patient support. However, the apparatus can be arranged to hold a coil in other orientations as, for example, at angles oblique to the longitudinal direction of the patient support. Desirable orientations for coils are discussed in greater detail in copending, commonly assigned U.S. Provisional Patent Application No. 60/327,329, filed Oct. 5, 2001, the disclosure of which is hereby incorporated by reference herein.

Figure 12:
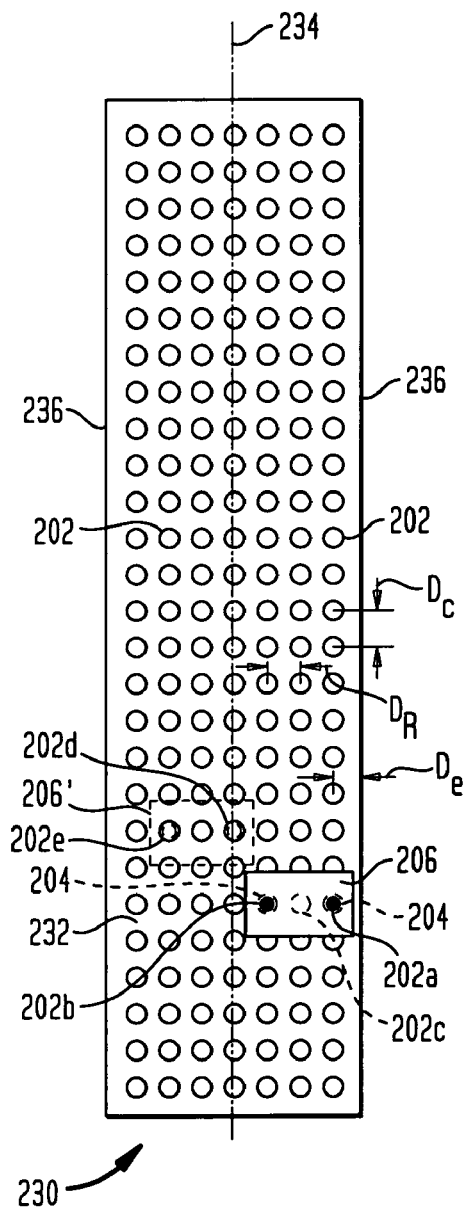
FIG. 12 is a diagrammatic plan view of a patient support incorporated in apparatus according to a further embodiment of the invention.

A system in accordance with a further embodiment of the invention includes a patient support 230, as shown in FIG. 12, in the form of an elongated table having a patient-receiving surface 232, lateral edges 236 and a direction of elongation 234 similar to the corresponding features of the patient support 130 discussed above with reference to FIGS. 8-10. In this embodiment, the fixture-positioning apparatus includes a large number of support attachment elements 202 in the form of holes extending into patient support 230 from the patient support surface 232. Support attachment elements or holes 202 are arranged in a rectilinear array with rows extending in the lateral direction, transverse to direction of elongation 234, and with columns extending in the longitudinal direction 234. The holes in the outermost columns of the array, closest to lateral edges 236 define an edge distance $D_E$ from the center of the holes in such columns to the adjacent edge 236 of the support. The holes 202 in each row are disposed at the same center-to-center distance or pitch $D_R$, which is uniform throughout the array. Also, the adjacent holes in each column are disposed at a pitch $D_C$, which is also uniform throughout the array, but which may or may not be equal to $D_R$.

Figure 13:
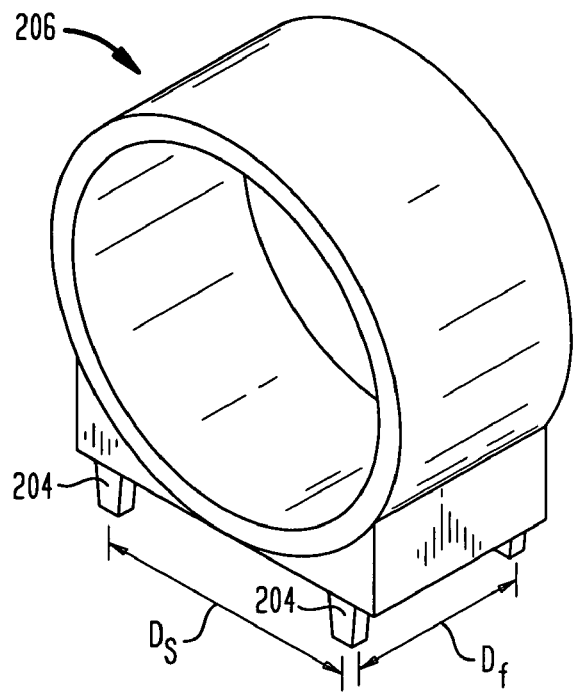
FIG. 13 is a diagrammatic perspective view of a fixture and associated components used with the patient support of FIG. 12.

The fixture-positioning apparatus also includes fixture attachment elements 204 (FIG. 13) mounted on a first fixture 206 to be used with the patient support. Thus, a first fixture 206 has a pair of fixture attachment elements 204 at a first spacing $D_S$ from one another. The spacing $D_S$ between the two pins 204 on the first fixture 206 is equal to an integral multiple of $D_R$, in this case twice $D_R$. Also, the distance $D_F$ from each pin 204 to the adjacent edge of the first fixture 206 is less than $D_E$. Thus, as shown in FIG. 12, the fixture attachment elements or pins 204 of the first fixture may be engaged with a set of support attachment elements or holes 202, including holes 202a and 202b, so as position the first fixture 206 at the location indicated in FIG. 12 in solid lines. Holes 202a and 202b constitute a first set of support attachment elements. The holes 202a and 202b constituting the first set of support elements are spaced apart from one another by twice $D_R$, i.e., an additional hole 202c is disposed between the holes 202a and 202b of this set.

Every other set of holes 202 spaced apart from one another by twice $D_R$ constitutes another set of support attachment elements which can receive the fixture attachment elements 204 on the first fixture 206. Thus, fixture 206 can be positioned at any one of many locations by engaging the fixture attachment elements or pins 204 on the first fixture with any similar set of support attachment elements or holes 202. For example, first fixture 206 can be positioned at position 206' shown in broken lines in FIG. 12 by engaging pins 204 with a set of holes 202d and 202e. However, because the distance $D_F$ from each pin 204 to the edge of fixture 206 is less than the edge distance $D_E$ from any hole 202 in the outermost row to the longitudinal edge 236 of the patient support, the first fixture 206 will always be disposed entirely between the longitudinal edges 236 of the patient support. As discussed above, this assures that the first fixture will not interfere with the gap-defining elements of the MRI apparatus during movement of the patient support.

Figure 14:
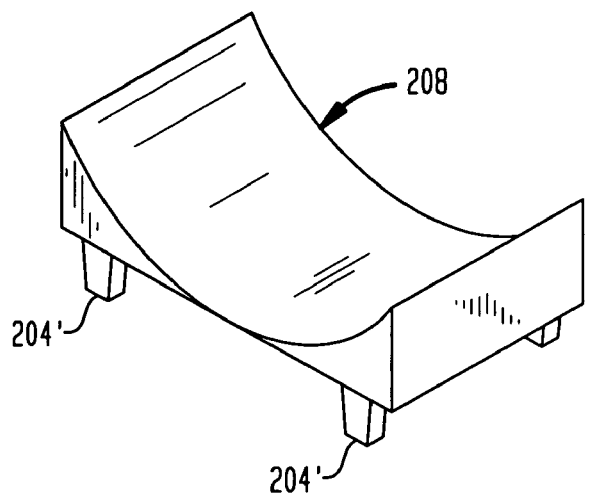
FIG. 14 is a diagrammatic perspective view of another fixture usable with the patient support of FIG. 12.

The system desirably includes one or more additional fixtures, such as a second fixture 208 (FIG. 14). The second fixture 208 has fixture attachment elements or pins 204' arranged in substantially the same way as the fixture attachment elements 204 of the first fixture, so that the second fixture can be engaged with a set of holes or support attachment elements to mount the second fixture to the patient support in addition to, or in lieu of, the first fixture. In a further variant, the spacing between the fixture attachment elements 204' of the second fixture can be different from the spacing between the fixture attachment elements of the first fixture, provided that this different spacing is an integral multiple of the row distance $D_R$ or the column distance $D_C$. For example, a relatively small fixture can be provided with pins 204' at a distance equal to $1 \times D_R$ or $1 \times D_C$. In a further variant, a very small fixture may have only one pin mountable in a set of support attachment elements consisting of only one hole 202.

The pins 204 are arranged to engage securely in holes 202. In the particular embodiment illustrated, the pins 204 are tapered, and each hole 204 has a mating taper. This arrangement may be similar to the common Morse taper fittings used in machine shop practice. In other variants, pins 204 can be provided with threads, and holes 202 may have mating threads. In yet another variant, the pins may be equipped with expansible elements or latches that can be engaged with mating fixtures around each hole 204. Essentially, any arrangement of mutually engagable parts which provides a secure attachment can be employed. In an alternative arrangement, the engageable elements can include strips of a hook and loop fastener on the fixture and on the patient support, these being arranged so that the range of fixture positions relative to the support is limited.

In yet another variant, the support can define a multiplicity of tracks similar to the track 46 defined by the mounting unit discussed above with reference to FIG. 2, and the fixture may have a foot similar to the base 52 of the fixture-positioning unit discussed above with reference to FIGS. 3 and 4. Desirably, these tracks extend in the lateral direction of the support and are disposed at spaced-apart locations along the length of the support.

Figure 3:
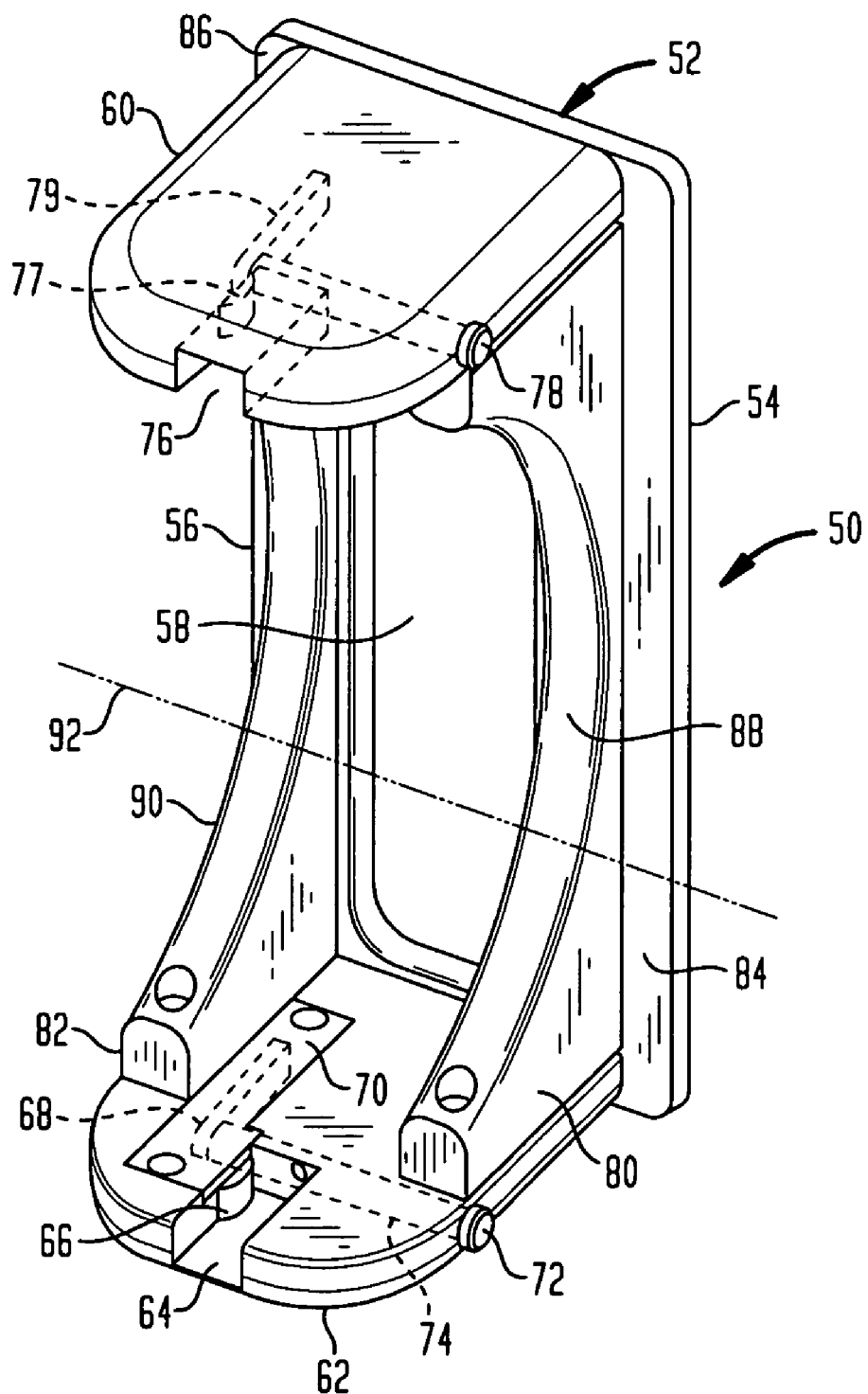
FIG. 3 is a diagrammatic perspective view of another component usable with the component of FIG. 1.

In a still further variant, a fixture-positioning unit as discussed with reference to FIGS. 3 and 4 can be used with a patient support defining multiple tracks.

Another aspect of the present invention includes a shoulder coil antenna fixture 500, as is shown in FIG. 15. As is explained in further detail below, the fixture 500 is another of the type of fixtures that may be advantageously mounted to the patient support 130. The positional flexibility afforded by patient-receiving surface 132 and mounting unit 20 allows the shoulder coil antenna 500 to be placed in close proximity to the region to be imaged thereby providing for a better scan of the region.

Figure 15A:
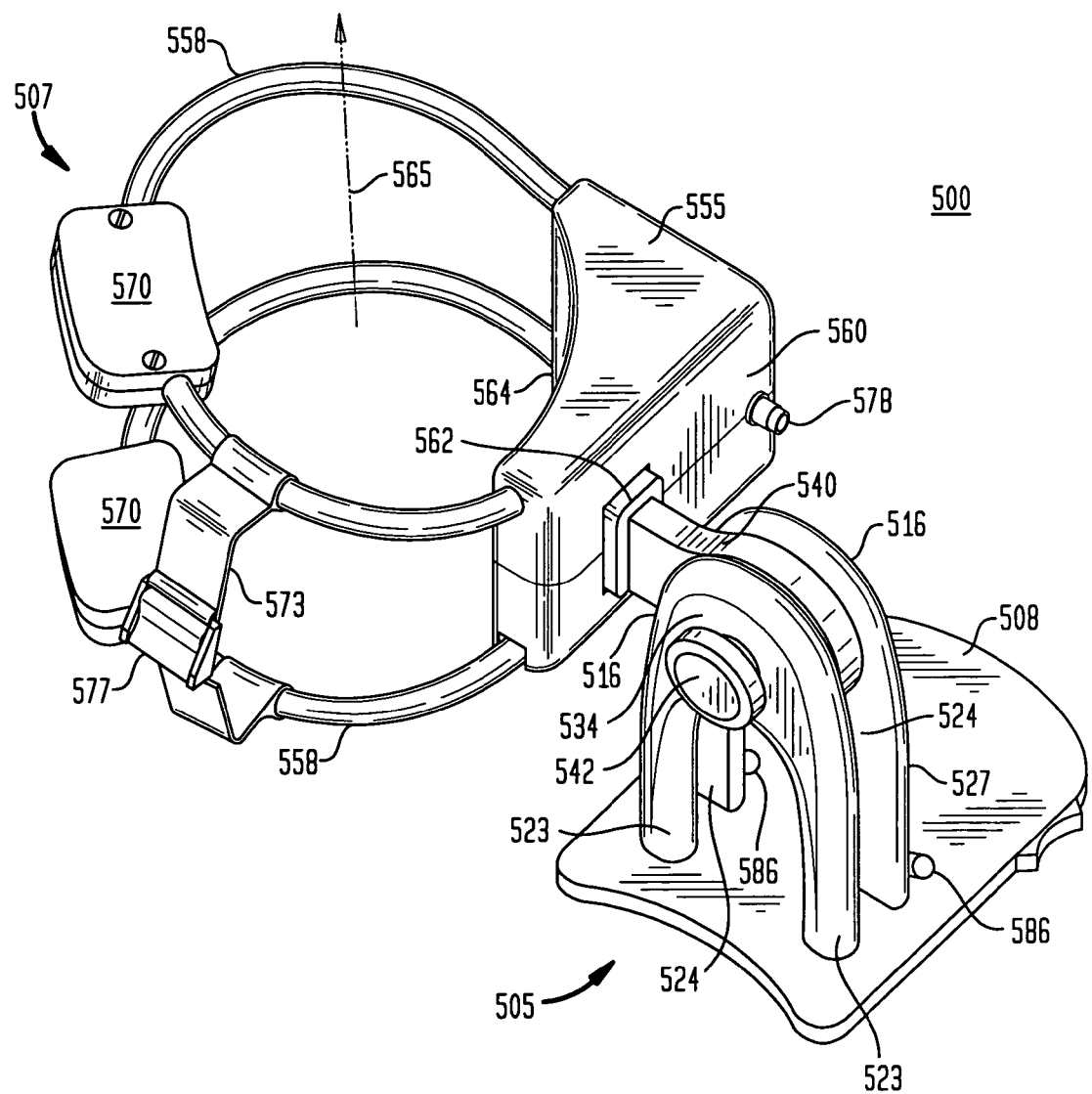
FIG. 15A is a perspective view of a shoulder coil antenna fixture in accordance with another aspect of the present invention.
Figure 15B:
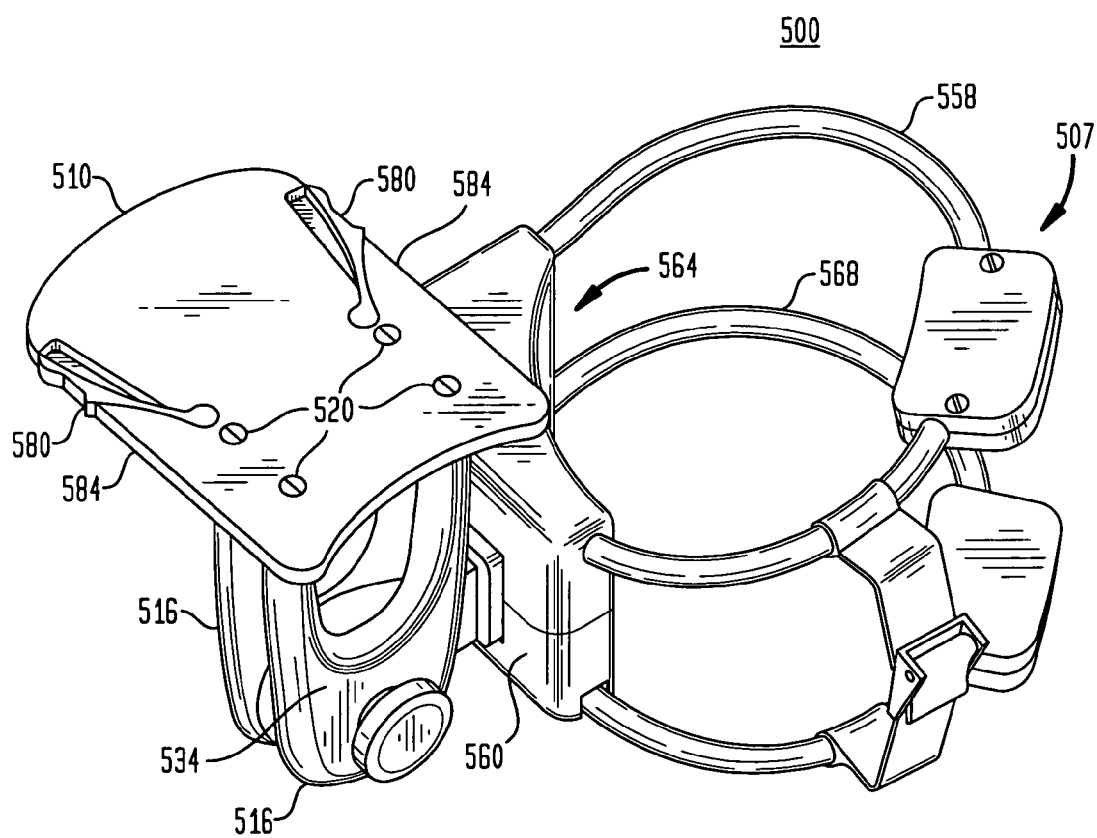
FIG. 15B is a rear perspective view of the fixture of FIG. 15A.

As is shown in FIG. 15A, the fixture 500 includes a base plate 505, which may be slidably mounted into the mounting unit 20, and an antenna assembly portion 507. The base plate 505 includes a top surface 508 and a bottom surface 510 (see FIG. 15B). Affixed to the top surface 508 are a pair of saddle shaped support members 516. The support members 516 may be affixed to base 505 using any number of fasteners including screws, rivets, pins, keys, lugs, etc. In accordance with this illustrative embodiment, FIG. 15B shows support members 516 being fastened to the base 505 by screws 520. The screws 520 are inserted through openings in the base 505 into the four legs 523 of members 516. Each leg 523 is appropriately threaded to accept the screw 520 and provide a secure connection. Legs 523 may be generally columnar in shape. However, in accordance with this embodiment, the legs include a substantially planar inner surface 524 terminating an outer columnar wall 527.

The top of members 516 is generally arched with the outer columnar walls 527 tapering into a planar outer surface 534. At the arch and between the space formed by the inner surfaces of the members 516, an arm 540 of the antenna assembly 507 is mounted. The arm 540 includes a donut-shaped end, which is pivotably or rotatably mounted to the members 516 preferably using a locking arrangement 542. The lock 542 may be advantageously tightened and loosened using the fingers thereby allowing the antenna portion 507 to be rotatably adjusted by a technician depending on the size and orientation of the patient. In addition to lock 542, other fasteners may be used to pivotably mount the arm 540 to members 516 including a manually operable cam, screw or locking element for forcibly engaging members 516 against arm 540.

The antenna portion 507 of the fixture 500 includes a base member 555 and a pair of coil windings 558. The base member 555 is a generally wedged-shaped element having a partially hollow interior. In the embodiment shown, the base member 555 has a first rectangular side wall 560 which is affixed to an end 562 of the arm 540. The end 562 may be affixed to the side wall using any number of fasteners. The base member 555 also includes a curved side wall 564, which is shaped so as to be advantageously placed on the shoulder of a patient.

The coil windings 558 each form a loop, a portion of which is threaded through the interior of base member 555. The base member 555 maintains the loops 558 in substantially parallel planes to each other. Note, however, that the loops need not be maintained in an exactly parallel position for the purposes of measurement. Each coil winding loop 558 forms an antenna having a field vector 565 that projects perpendicular to an imaginary planar surface of the coil loops 558. Each coil loop 558 is also coupled to an enclosure 570 through which each coil loop 558 is threaded. The enclosures 570 functions to keep the coil loops 558 close to the surface of a patient during imaging. The coil loops 558 are also coupled together by a magnetically translucent strap 573. The strap 573 is attachable at a buckle 577, which may comprise a plastic clip or mating strips of Velcro. The straps 573 further serve to keep the fixture in place during imaging.

A connector 578 is connected to the first side wall 560. The connector 578 may be a coaxial, triaxial, D-type, SMA or any other type of connector suitable for coupling the signals transmitted or received by the coils 558 between the coil 558 and other ancillary equipment necessary to perform the imaging process. In another embodiment the connector 578 may be replaced by a cable permanently connected to the coils.

FIG. 15B shows another perspective view of the fixture 500, in particular showing the bottom surface 510. A pair of control latches 580 are movably mounted to bottom surface 510 so as to exert a force outwards towards the long edges 584 of the base 505. The outward force maintains the fixture 500 in place, even with the patient support 130 in a vertical position. The latches are mounted using springs (not shown) that may be controlled by knobs 586 (see FIG. 15A). In the embodiment shown, the depression of knobs 586 cause the latches 580 to retract inward away from the edges 584 thereby allowing the fixture 500 to be removed from the mounting support 20.

Figure 16A:
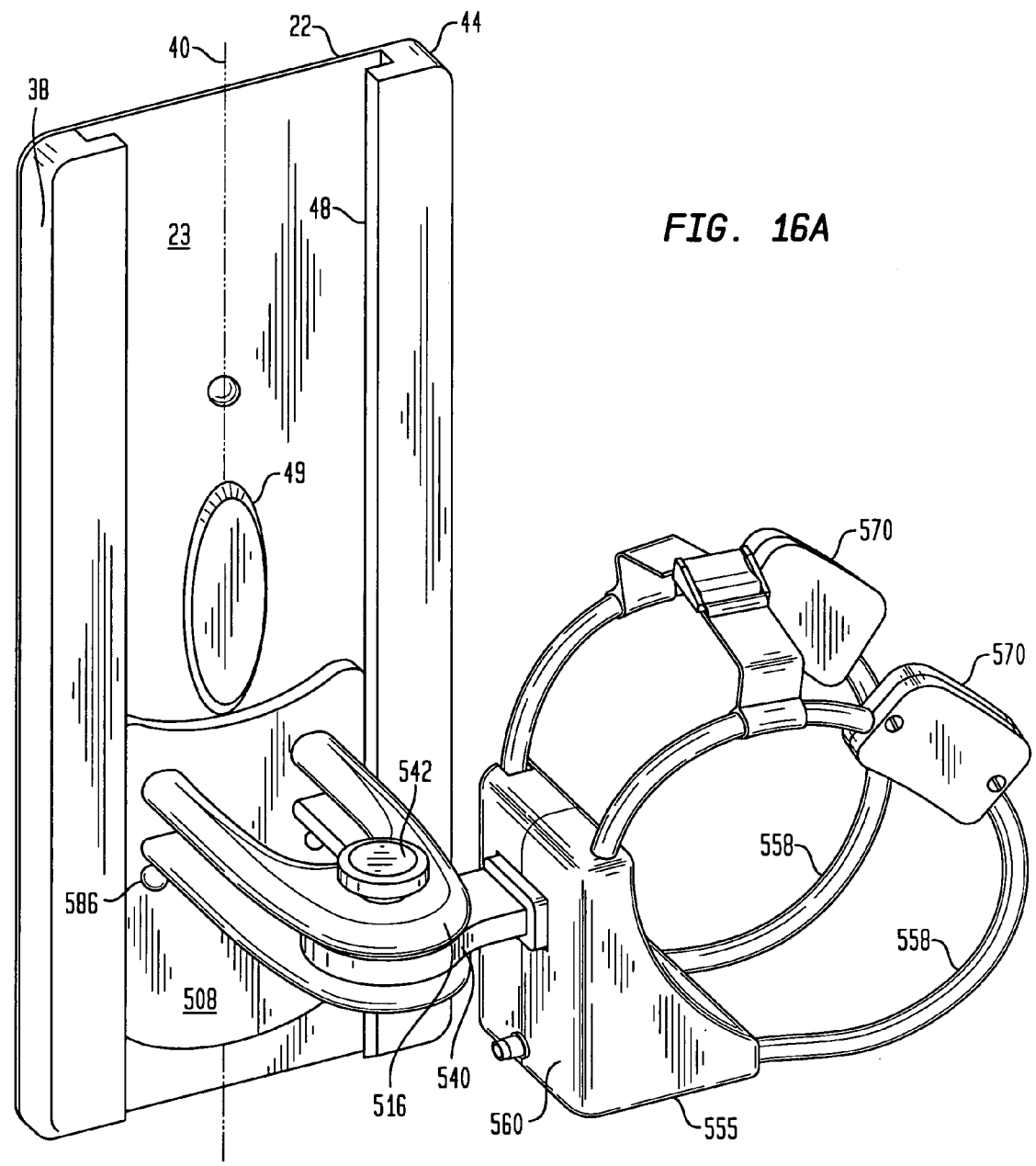
FIG. 16A is a front perspective view of the fixture and the mounting component.

In particular, as shown in FIG. 16A, the fixture 500 is slidably mounted into mounting support 20 such that the long edges of the base 505 are substantially parallel to track direction 40. In addition to control latches 580, the stop 49 also serves to hold the fixture 500 in place during imaging. As previously stated, by pressing knobs 586, the fixture 500 may be removed from mounting unit 20 by sliding the base 505 away from stop 49. FIG. 16B shows a rear perspective view of the fixture 500 and mounting unit 20 when engaged.

Figure 17:
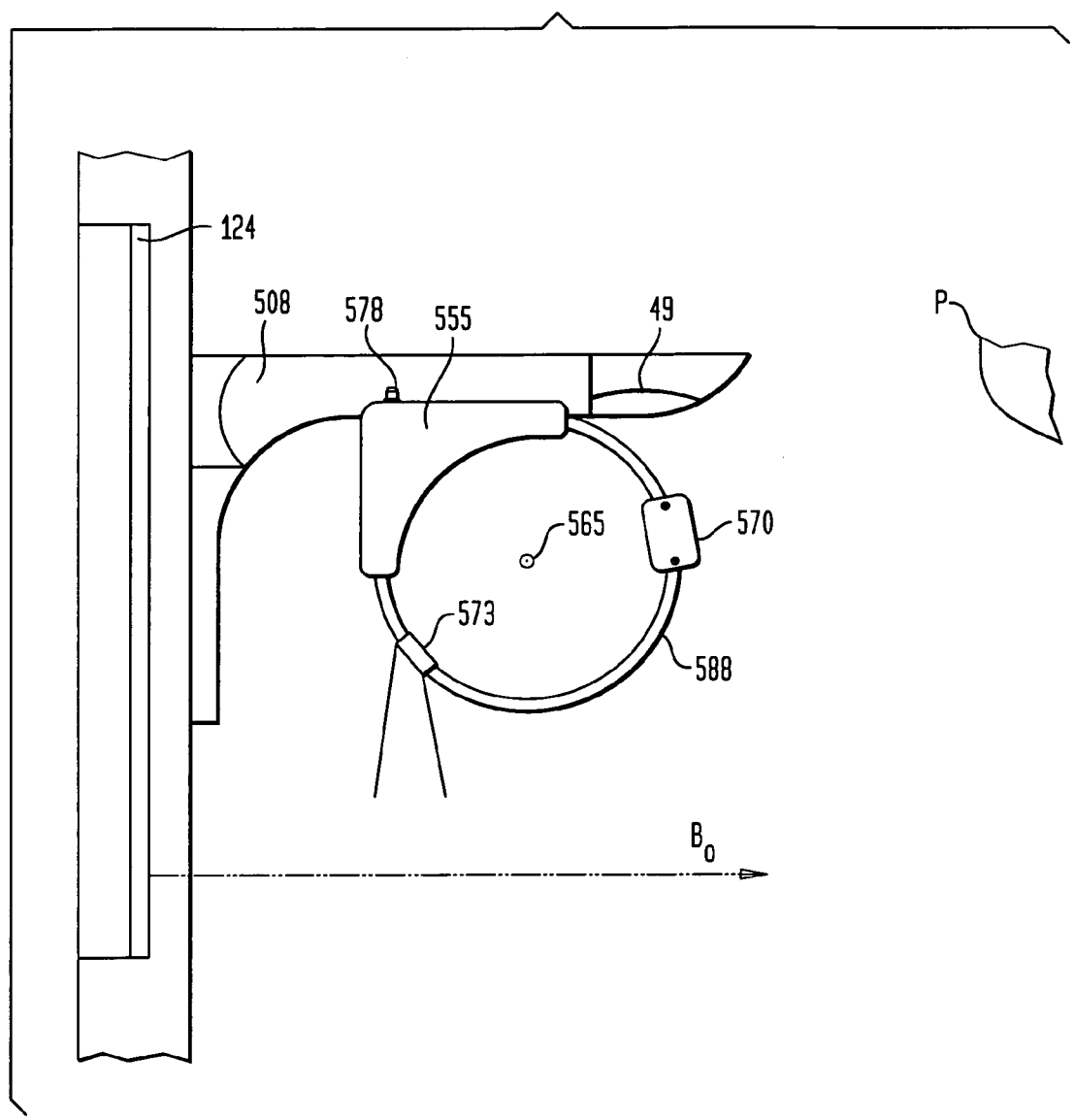
FIG. 17 is a partial detailed front view of a patient fitted with the shoulder coil antenna fixture.

Turning now to FIG. 17, there is shown an illustrative view of a patient being imaged in accordance with an aspect of the present invention. Patient P is fitted with the coils 588 of the fixture 500 snugly placed over the shoulder. As shown, the fixture 500 saddles the shoulder region with the respective antenna coils being positioned at the anterior and posterior surface of the patient's anatomy. The strap 573 is positioned to go under the patient's underarm and is adjusted to keep the coils 588 against the patient's P shoulder. The field vector 565 of the coils 588 is orthogonal to the static magnetic field vector $B_0$ and therefore can receive the magnetic resonance signals generated by the atomic nuclei. In accordance with the present invention, the placement of the antenna in close proximity to the region being imaged increases the quality of the images taken. In addition, it is possible to design an antenna structure having a plurality of coils at the anterior or posterior surface of a patient. Such an arrangement would further enhance the signal-to-noise ratio of the antenna thereby resulting in improved imaging capability.

The saddle shape feature of device 500 is also particularly advantageous in imaging and supporting other regions of the anatomy. In particular, such advantages are realized because a device may be contoured to fit or saddle a particular region of interest of the anatomy. In addition, where the antennas are arranged to form coil pairs, as for example the antennas of device 500, the antennas may be placed close to the region of interest and receive resonance signals that emanate from both or either of the posterior and/or anterior surface(s) of the patient. Such a coil pair may take the electrical and magnetic form of a Helmhotz pair, a volume phased array, a saddle coil and other antenna forms known in the art.

Devices of this type are advantageous in a magnetic resonance imaging apparatus that supports a patient in a substantially upright position (such as apparatus 120) as they may be placed adjacent to one or more regions of the patient's anatomy with the patient in a substantially upright weight-bearing or gravity effecting position. That is, the devices are held in place even as the patient support of the apparatus is positioned to orient the patient in a standing or sitting position.

In addition, the devices disclosed herein tend to reduce the anxiety of the patient. In particular, where prior art devices tend to wrap around or be coaxial with a patient's anatomy, devices implemented in accordance with this aspect of the invention employ a saddle shape that is not coaxial with the patient's anatomy. Because the devices are localized and rest substantially against only the region of anatomical interest, a patient will tend to notice them less and be more relaxed. Furthermore, when employed in an antenna assembly the devices allow for an improvement in imaging capability.

As a general matter and in accordance with another aspect of the present invention, such antennas may be realized for imaging any portion or organ of the human anatomy. Such other devices may be implemented in accordance with the present invention by contouring the base member 555 to suit the region of the body where imaging needs to be performed. Such a base member may be oriented relative to the portion of the patient's anatomy to be imaged so that at least one antenna is adjacent to surface of the patient's anatomy, such as the anterior or posterior surfaces.

For example, for imaging of organs or tissue on the torso, the curved side wall 564 of base member 555 may be replaced by a rectangular side wall substantially parallel to side wall 560. The width of the base member (extending in a direction substantially parallel to vector 565) would need to extend to accommodate the anterior to posterior size of a typical patient. The radius of the loop antennas 558 could also be increased to cover a larger area. In addition, loop antennas of different radii could be arranged substantially co-centrically about the region of interest since member 555 would include a larger surface area and interior portion to accommodate more loop antennas. Of course with larger structures, the base 505 may need to be extended to its maximal length and include an opening to accommodate stop 49. Alternatively, the entire structure may comprise an entire unit that mounts onto the patient receiving surface 132 in much the same way mounting unit 20 engages the patient receiving surface 132.

In a further variant, a saddle shaped device may be constructed in accordance with the present invention by again modifying the base member 555 to generally fit the top of a human head. The base member 555 may also be modified to fit between the legs of a patient so as to obtain images of the pelvic floor which are important in detecting prostate or ovarian cancer.

In another variant, the base plate 505 along with elements 516 and 540 need not be included as part of the structure of the devices disclosed herein. In particular, where the patient is imaged in a substantially horizontal position, the weight of the base member alone along with straps similar to straps 573 may be sufficient to maintain such saddle shaped devices in place.

Figure 18A:
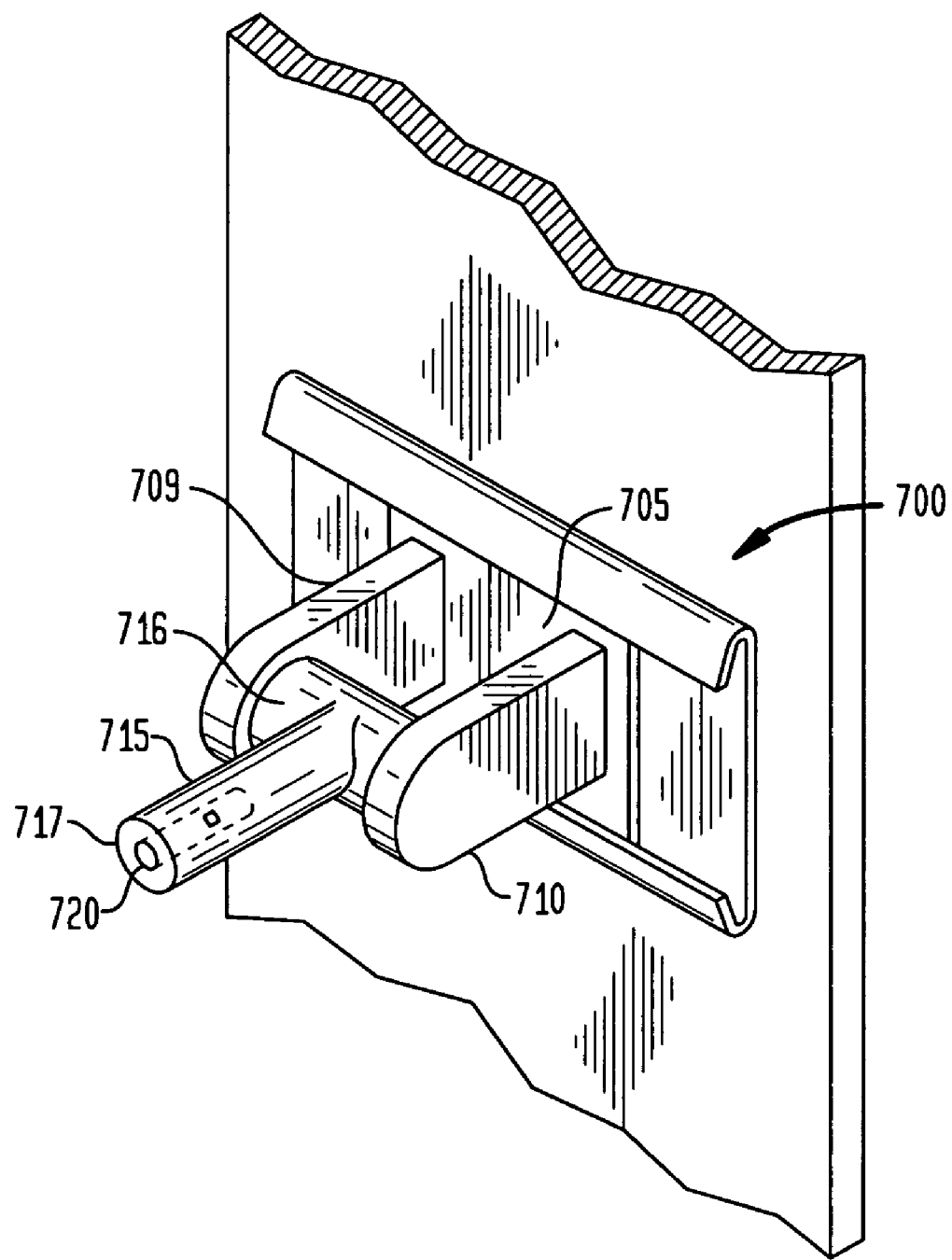
FIG. 18A is a schematic of a universal arm in accordance with another aspect of the present invention.

In accordance with another aspect of the present invention, FIG. 18A depicts a universal arm 700 for use in conjunction with a stand-up magnetic resonance imaging apparatus such as apparatus 120. The universal arm 700 is usable with a number of devices, such as antennas, heart monitors, oxygen monitors, etc. that may be used during magnet resonance imaging. The arm 700 comprises a base 705 from which projects a pair of support members 709 and 710. The support members may be constructed as is described above in relation to saddle shaped support member 516. Alternatively, the support members 709 and 710 may form a unitary structure with base 705. A base arm member 715 is rotatably mounted between the support members 709 and 710 at its proximate end 716 such that the arm member 715 rotates along the longitudinal direction 134. The base arm member 715 may be mounted as is described above in relation to device 500.

The universal arm 700 may be slidably mounted into mounting unit 20 as is shown in FIG. 18A, alternatively the universal arm 700 may comprise a single unit that is attached to the support surface 132 as is described above in relation to mounting unit 20. In a further variant the universal unit may also be adapted to fit into the patient support 230 as is shown in FIG. 12.

At its distal end 717 the arm 715 is constructed to be adaptable to receive devices that may be used in imaging the patient. In an embodiment, the distal end 717 includes an opening 720 of a predetermined depth that is adaptable to receive devices such as an antenna assembly. In accordance with this embodiment the antenna assembly would be inserted into the opening 720 at the distal end such that the antenna assembly would be locked in place using, for example, the latching assemblies described hereinabove. Alternatively, the distal end of the arm 715 may be arranged to provide a pivot point for devices or antenna assemblies attached thereto.

Figure 18B:
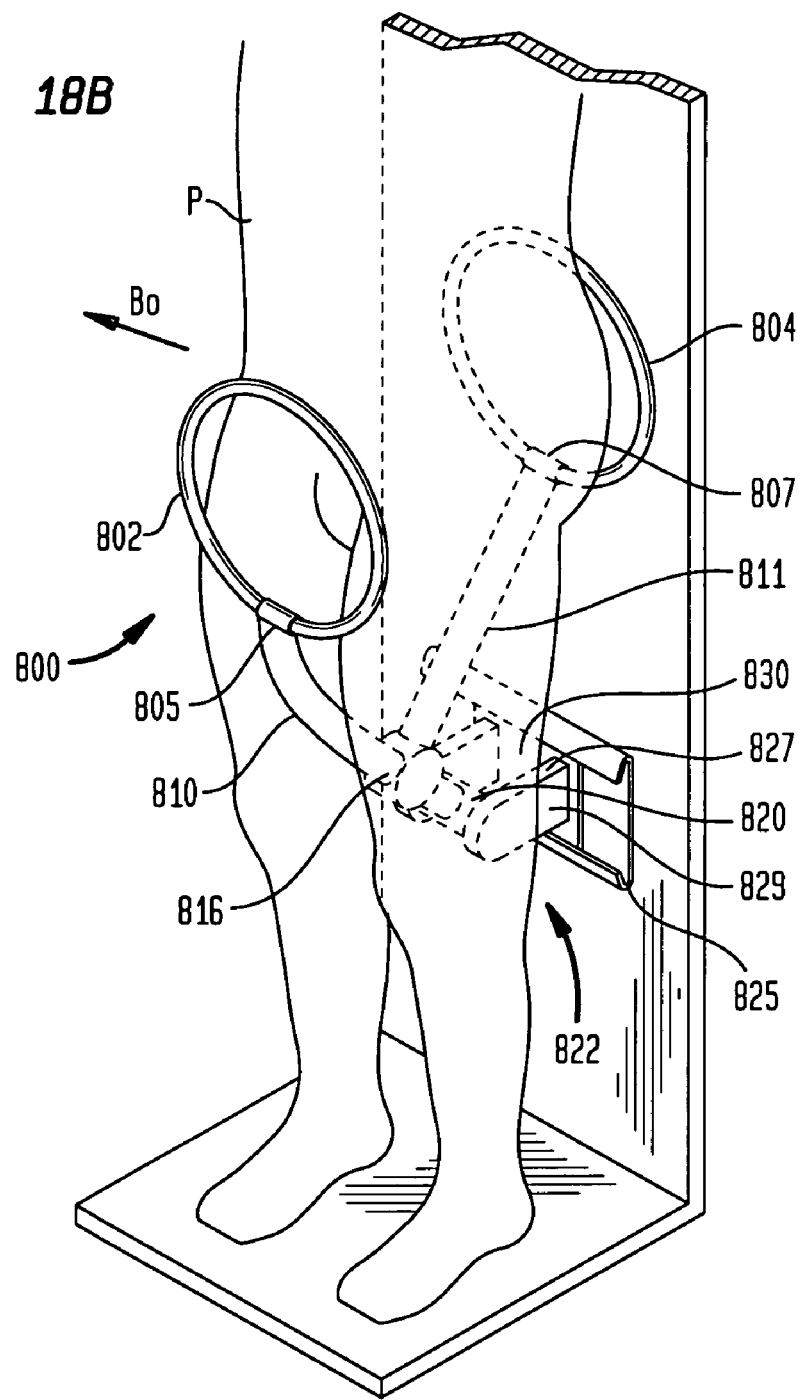
FIG. 18B is partial detailed perspective view of a patient fitted with an antenna assembly in accordance with an embodiment of the present invention.

In particular, FIG. 18B illustratively depicts an embodiment of a device 800 useful in imaging the pelvic region of a patient P in accordance with this aspect of the present invention. The device 800 comprises a first coil antenna 802 and a second coil antenna 804. The first coil antenna 802 is adjacent to the anterior surface of the patient P while the second coil antenna is adjacent to the posterior surface of the patient P. Each antenna 802, 804 is threaded through an end 805, 807 of respective support arms 810, 811. The support arms are rotatably mounted at a pivot point 816. In this embodiment the pivot point 816 is formed by mounting the support arms 810, 811 to a base arm 820. The support arms 810, 811 and base arm 820 may be pivoted about each other in a number of ways, including the pivot and locking mechanism already described above for device 500. In addition, the pivot point may be formed in an assembly where support arm 810 and base arm 820 form one structure to which support arm is pivotably attached.

An end 822 of base member 820 is mounted to a base 825. The base 825 includes a pair of projections 827, 829 from base support 830 which may be slidably mounted into support 20. As previously discussed, the assembly may also be constructed such that the base and mounting unit form a unitary structure adaptable to the patient support surface. In a preferred embodiment the end 822 is pivotably mounted between the projections 827, 829. However, it is also possible to fixably mount the end 822 between the projections 827, 829 because the rotation of support arms 810, 811 along with the slotted design of the support surface will allow adjustment of the antennas to rest against the anterior and posterior surfaces of the vast majority of patients.

Figure 18C:
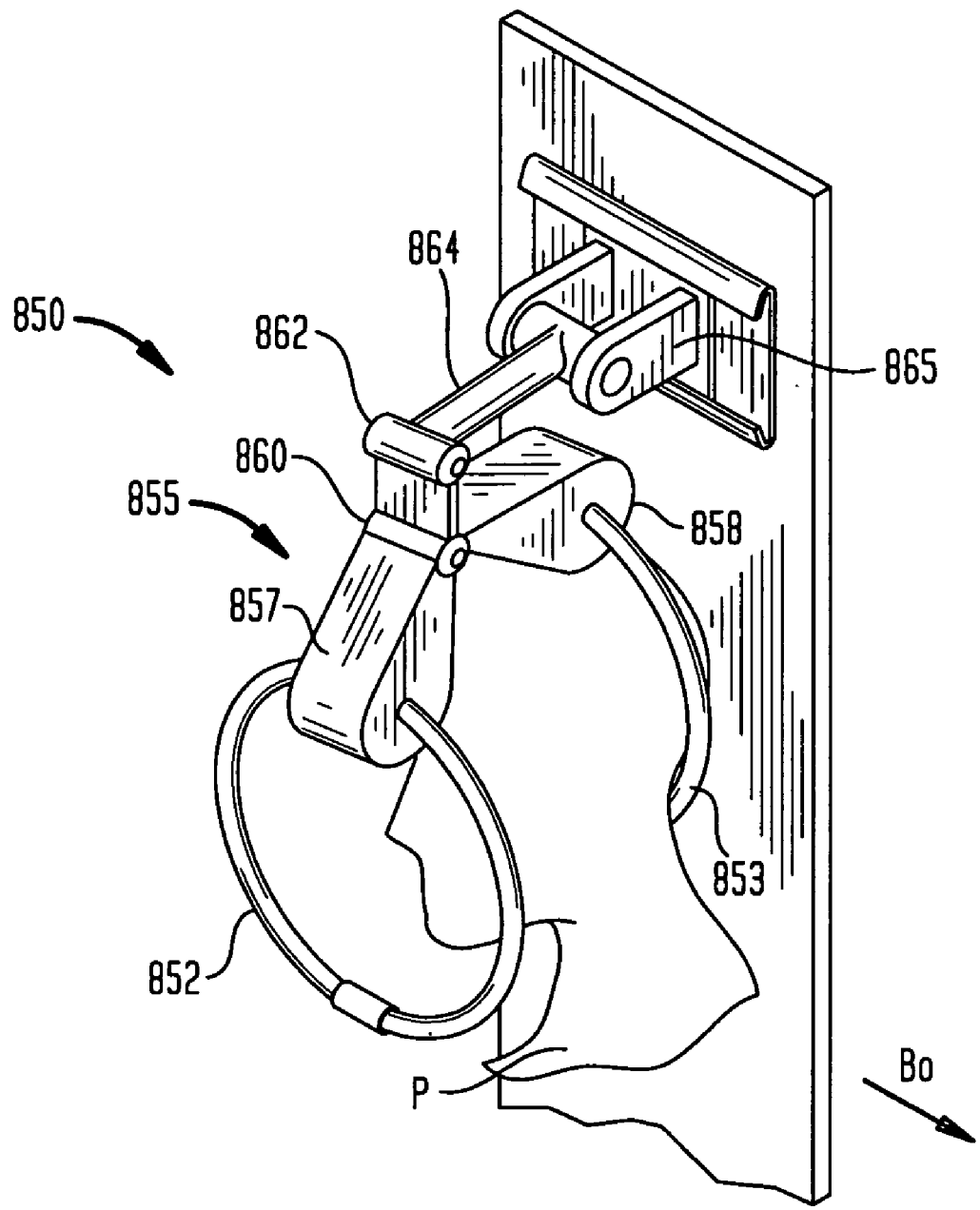
FIG. 18C is partial detailed perspective view of a patient fitted with another antenna assembly in accordance with an embodiment of the present invention.

FIG. 18C illustratively depicts a device 850 for use in imaging the head. The device 850 comprises a pair of loop coil antennas 852, 853 that are threaded through a support member 855. In particular, loop coil antenna 852 is threaded through a first finger member 857 of the support member 855. The loop coil antenna 853 is threaded through a second finger member 858. The finger members 857, 858 are mounted together at a point 860. The point 860 is preferably pivotable to allow the finger members 857, 858 to be adjusted so that the antennas 852 and 853 may be placed in close proximity to the back or front (face) of the patient's P head.

The device 850 may also include a second pivot point 862, which is shown attached to an arm 864. The arm 864 is shown as being connected to a base 865 similar to base 825 described previously. The base 865 may likewise be slidably mountable into mounting unit 20.

Figure 18D:
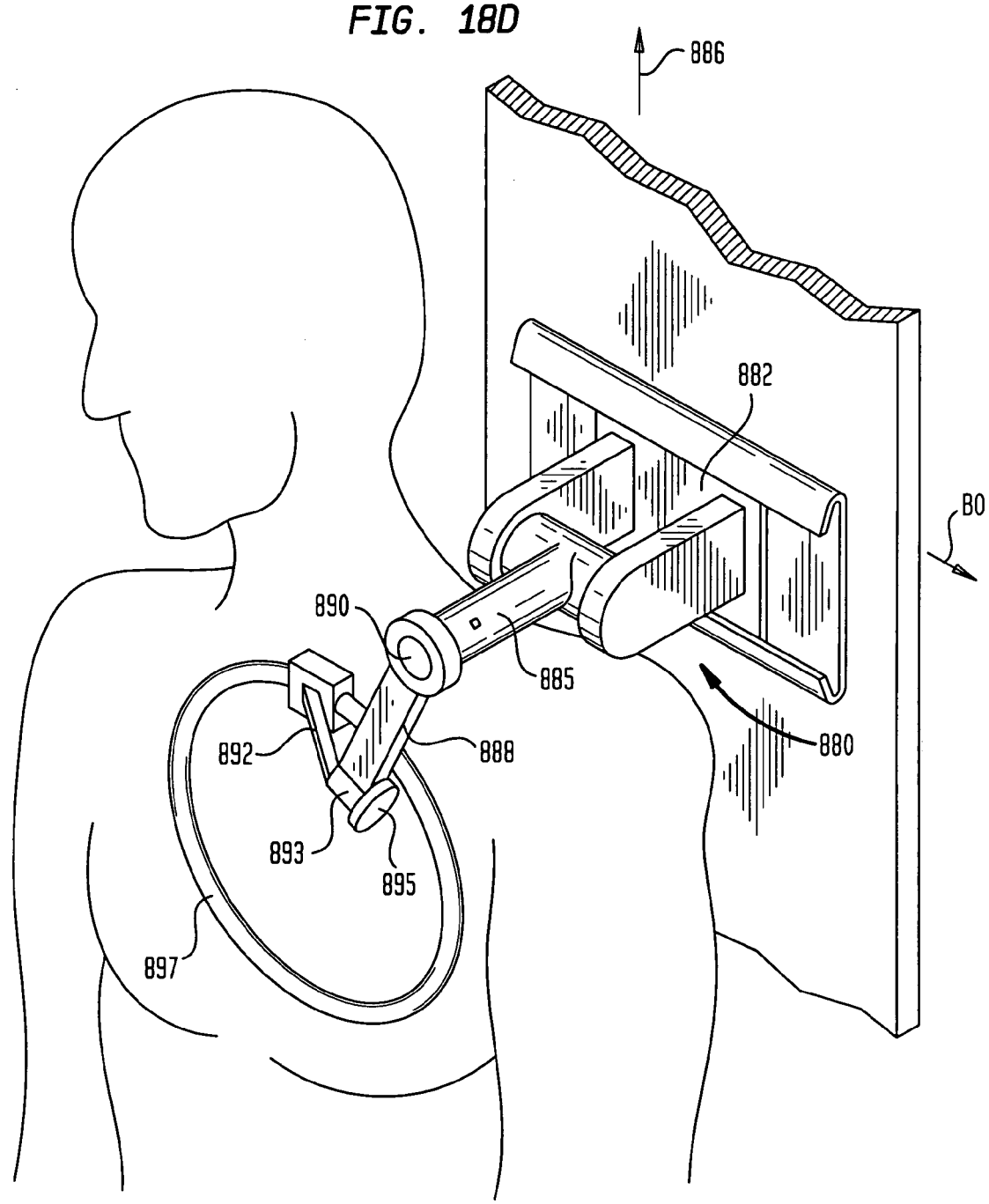
FIG. 18D is partial detailed perspective view of a patient fitted with another antenna assembly in accordance with an embodiment of the present invention.

FIG. 18D shows an embodiment of a device 880 adapted for imagining the chest region of a patient P. The device 880 includes a base member 882, similar to base members 825 and 865 and which is mountable into mounting unit 20. The device 880 further comprises a first arm member 885 that is connected to base member 882. As shown, the first arm member 882 allows for rotation in at least a direction along the longitudinal axis 886 of the patient P, which is parallel to longitudinal direction 134. First arm member 885 is pivoted about a second arm member 888 at a pivot point 890. As shown the pivot point 890 allows the second arm member 888 to rotate around the first arm member 885.

An antenna support arm 892 is connected at a distal end 893 of second arm member 888. The antenna support arm is locked in placed by locking mechanism 895, which may be similar to the locking mechanisms described hereinabove. The locking mechanism may be loosened by a technician to allow positioning of the antenna 897 to be adjusted to the region to be imaged on the torso. The antenna 897 is threaded through the support arm 892.

The device 880 is shown as including only a single loop coil antenna 897, however a second antenna may attached to arm 885 in a manner similar to that discussed in relation to FIG. 18C. In addition, although FIGS. 18B and 18C show two antennas in the disclosed embodiment, a single antenna may be suitable for obtaining the images desired. In particular, in either FIGS. 18B or 18C, a device may be constructed that includes either of the posterior or anterior antennas.

As these and other variations and combinations can be employed, the foregoing description of the preferred embodiments should be taken by way of illustration rather than by way of limitation of the invention as defined by the claims.

The invention claimed is:

1. A system for magnetic resonance imaging comprising:
a magnetic resonance imaging apparatus having a structure including opposed elements defining a patient receiving space and a patient support movable relative to said structure through a range of support positions;
a mounting apparatus; and
a fixture connected to said magnetic resonance apparatus, said mounting apparatus being operative to secure the fixture to the patient support and to permit slidable adjustment of the position of the fixture relative to the patient support over a range of fixture positions and said fixture including a base plate and an antenna assembly having a base member pivotably mounted to said base plate and including at least one coil antenna in the shape of a loop that is threaded through said base member.

2. The system of claim 1 wherein said base member is pivotably mounted to said base plate by a pair of saddle shape members and an arm having a donut shaped end, said donut shaped end of said arm being pivotably mounted between said saddle shape members.

3. The system of claim 1 wherein said base plate further comprises a pair of control latches mounted to a bottom surface of said plate and wherein said control latches function to hold the fixture in position when said base plate is engaged with said mounting apparatus.

4. The system of claim 1 wherein said mounting apparatus defines a track direction that is adapted to engage with said patient support such that said track direction is substantially traverse to a longitudinal direction of the patient support.

5. The system of claim 4 further comprising detents arranged to hold said mounting apparatus at predetermined locations along said track direction.

6. A method for operating a magnetic resonance imaging apparatus comprising:
positioning a fixture on a patient support of a magnetic resonance apparatus using a mounting device, the fixture including a base plate and an antenna portion having a base member pivotably mounted to the base plate and a pair of coil windings forming a first loop and a second loop, the first and second loops being threaded through the base member such that the first and second loops can be maintained in substantially parallel planes as the base member pivots about the base plate; and
positioning a patient on the patient support such that an anatomical area interest associated with the patient is saddled by the fixture.

7. The method of claim 6 further comprising moving the patient support within a range of support positions between a pair of magnet elements defining a gap.

8. The method of claim 6 wherein positioning the fixture includes engaging positioning elements on the fixture with mating elements on the patient support.

9. The method of claim 6 wherein the anatomical area of interest is a shoulder of the patient.

10. A fixture for a magnetic resonance imaging apparatus, comprising:
a base plate; and
an antenna portion having a base member pivotably mounted to said base plate and including a pair of coil windings forming a first loop and a second loop, said first and second loops being threaded through said base member such that said loops can be maintained in substantially parallel planes as said base member pivots about said base plate,
said base member being pivotably mounted to said base plate by a pair of saddle shape members and an arm having a donut shaped end, said donut shaped end of said arm being pivotably mounted between said saddle shape members.

11. The fixture of claim 10 wherein said base plate further comprises a pair of control latches mounted to a bottom surface of said base plate.

12. A system for magnetic resonance imaging, the system comprising:
a magnetic resonance imaging apparatus having a structure including a magnet having opposed elements defining a patient-receiving space therebetween, a magnet axis extending substantially horizontally and a patient support disposed within said patient-receiving space capable of supporting a patient in a substantially upright position; and
a support arm comprising a base member,
said support arm mounted to said patient support such that said support arm projects from said patient support in a direction substantially transverse to a longitudinal direction of said patient support,
said support arm being slidably mounted to a mounting unit and said mounting unit being adapted to engage said patient support, and
at least one support member projecting from a surface of said base member and an arm mounted to said at least one support member, said arm being rotatable in a direction substantially transverse to the direction of said magnet axis, at least one support arm mounted to a distal end of said arm and a loop antenna coil threaded through an opening at a distal end of said at least one support arm.

13. A system for magnetic resonance imaging, the system comprising:
a magnetic resonance imaging apparatus having a structure including a magnet having opposed elements defining a patient-receiving space therebetween, a magnet axis extending substantially horizontally and a patient support disposed within said patient-receiving space capable of supporting a patient in a substantially upright position; and
a support arm comprising a base member,
said support arm mounted to said patient support such that said support arm projects from said patient support in a direction substantially transverse to a longitudinal direction of said patient support,
said support arm being slidably mounted to a mounting unit and said mounting unit being adapted to engage said patient support, and
at least one support member projecting from a surface of said base member and an arm mounted to said at least one support member, said arm being rotatable in a direction substantially transverse to the direction of said magnet axis, at least one support member mounted to a distal end of said arm, said support member including at least one finger member thorough which is threaded a loop coil antenna.

14. A system for magnetic resonance imaging, the system comprising:
a magnetic resonance imaging apparatus having a structure including a magnet having opposed elements defining a patient-receiving space therebetween, a magnet axis extending substantially horizontally and a patient support disposed within said patient-receiving space capable of supporting a patient in a substantially upright position; and
a support arm comprising a base member,
said support arm mounted to said patient support such that said support arm projects from said patient support in a direction substantially transverse to a longitudinal direction of said patient support, said support arm being slidably mounted to a mounting unit and said mounting unit being adapted to engage said patient support, and at least one support member projecting from a surface of said base member and an arm mounted to said at least one support member, said arm being rotatable in a direction substantially transverse to the direction of said magnet axis, at least one support arm having a distal end to which is attached an antenna support arm having a loop antenna threaded there-through.

* * * * *